US011859145B1

(12) United States Patent
Hegg et al.

(10) Patent No.: US 11,859,145 B1
(45) Date of Patent: Jan. 2, 2024

(54) ECONOMICAL METHODS FOR PERFORMING OXIDATIVE CATALYTIC PRETREATMENT OF PLANT BIOMASS USING A SINGLE-STAGE TWO OXIDANT PROCESS

(71) Applicants: Board of Trustees of Michigan State University, East Lansing, MI (US); Montana State University, Bozeman, MT (US); Wisconsin Alumni Research Foundation, Madison, WI (US)

(72) Inventors: Eric L. Hegg, East Lansing, MI (US); Zhaoyang Yuan, Ottawa (CA); David B. Hodge, Bozeman, MT (US); Shannon S. Stahl, Madison, WI (US); Bryan D. Bals, Indianapolis, IN (US)

(73) Assignees: Board of Trustees of Michigan State University, East Lansing, MI (US); Montana State University, Bozeman, MT (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/897,566

(22) Filed: Aug. 29, 2022

(51) Int. Cl.
*C10L 1/02* (2006.01)
*B01J 23/04* (2006.01)
*B01J 27/055* (2006.01)

(52) U.S. Cl.
CPC ............... *C10L 1/02* (2013.01); *B01J 23/04* (2013.01); *B01J 27/055* (2013.01); *C10L 2200/0484* (2013.01)

(58) Field of Classification Search
CPC ...... C10L 1/02; C10L 2200/0484; B01J 23/04; B01J 27/055
See application file for complete search history.

(56) References Cited

U.S. PATENT DOCUMENTS

2008/0139841 A1\* 6/2008 Givens .................. C07C 51/265
562/407
2013/0045509 A1 2/2013 Romero
(Continued)

FOREIGN PATENT DOCUMENTS

| CA | 2163389 A1 | 5/1996 | |
| WO | 2006/121634 A2 | 11/2006 | |
| WO | WO-2006121634 A2 \* | 11/2006 | ............... D21C 1/02 |

OTHER PUBLICATIONS

Hodge et al. (Biotechnology and Bioengineering, 2013, 110(4), 1078-1086) (Year: 2013).\*
(Continued)

*Primary Examiner* — Ellen M McAvoy
*Assistant Examiner* — Chantel Graham
(74) *Attorney, Agent, or Firm* — Westman, Champlin & Koehler, P.A.; Amanda M. Prose

(57) ABSTRACT

An improved alkaline pretreatment of biomass is provided that is a single-stage, two oxidant alkaline oxidative pretreatment process. The process uses a homogenous catalyst with at least two oxidants (Hydrogen peroxide and enhanced levels of oxygen) in an alkaline environment to catalytically pretreat lignocellulosic biomass in a single-stage oxidation reaction. The provided single-stage alkaline-oxidative pretreatment improves biomass pretreatment and increase enzymatic digestibility to improve the economic feasibility of production of lignocellulose derived sugars.

20 Claims, 8 Drawing Sheets

(56) References Cited

U.S. PATENT DOCUMENTS

2016/0168796 A1* 6/2016 Hamed ............... D21H 17/64
162/14
2020/0332376 A1 10/2020 Hegg et al.

OTHER PUBLICATIONS

Upton, B.M. et al. "Strategies for the conversion of lignin to high-value polymeric materials: review and perspective" Chem Rev. 2016;116(4):2275-306.

Van Heiningen et al., A chemical reactor analysis of industrial oxygen delignification. Pulp Paper Canada. 2003, 104 (12), 96.

Van Heiningen et al. "Recent progress on oxygen delignification of softwood kraft pulp. Cellulose science and technology: chemistry, analysis, and applications" In: Cellulose Science and Technology, Wiley & Sons, 2018.

Van Heiningen et al. "Selectivity Improvement During Oxygen Delignification by Adsorption." 2003. J Pulp Paper Sci. 29, 48.

Wang, H.M. et al. "Advanced and versatile ligninderived biodegradable composite film materials toward a sustainable world" Green Chem. 2021;23:3790-817.

Yoo, C.G. et al. "The critical role of lignin in lignocellulosic biomass conversion and recent pretreatment strategies: a comprehensive review" Bioresour Technol. 2020;301: 122784.

Yuan, Z. et al. "Effective biomass fractionation through oxygen-enhanced alkaline-oxidative pretreatment" ACS Sustain Chem Eng. 2021;9:1118-27.

Yuan, Z. "Integrated two-stage alkaline-oxidative pretreatment of hybrid poplar. Part 2: impact of Cu-catalyzed alkaline hydrogen peroxide pretreatment conditions on process performance and economics" Ind Eng Chem Res. (2019) 58:16000-8.

Zhang, R. et al. "Facile synthesis of vanillin from fractionated Kraft lignin" Ind Crop Prod. (2020) 145: 112095.

Zhang, Y. et al. "High solid content production of environmentally benign ultra-thin lignin-based polyurethane films: plasticization and degradation" Polymer (2019) 178: 121572.

Alherech, M. et al. "From Lignin to Valuable Aromatic Chemicals: Lignin Depolymerization and Monomer Separation via Centrifugal Partition Chromatography" ACS Cent. Sci. 2021, vol. 11, pp. 1831-1837.

Alinejad M, et al. "Lignin-based polyurethanes: opportunities for bio-based foams, elastomers, coatings and adhesives" Polymers. 2019;11(7):1202.

Alvarez-Vasco, C., et al. "Alkaline hydrogen peroxide pretreatment of softwood: Hemicellulose degradation pathways" Bioresource Technology (2013) 150, 321-327.

Bajwa D.S., et al. "A concise review of current lignin production, applications, products and their environmental impact" Ind Crops Prod. 2019;139: 111526.

Banerjee, G. et al. "Effects of Biomass, Peroxide, and Enzyme Loading and Composition on Yields of Glucose and Xylose" Biotechnol Biofuels 2011, 4:16.

Bhalla, A, "Effective alkaline metal-catalyzed oxidative delignification of hybrid poplar" Biotechnol Biofuels. 2016;9:34:1-10.

Bhalla, A. et al. "Engineered lignin in poplar biomass facilitates Cu-catalyzed alkaline-oxidative pretreatment" ACS Sustain Chem Eng. 2018;6(3):2932-41.

Bhalla, A, et al. "Performance of three delignifying pretreatments on hardwoods: hydrolysis yields, comprehensive mass balances, and lignin properties" Biotechnol Biofuels. 2019;12(1):1-5.

Bourbiaux D. et al. "Reductive or oxidative catalytic lignin depolymerization: an overview of recent advances" Catal Today. 2021;373:24-37.

Brandt, A.; Chen, L.; van Dongen, B. E.; Welton, T.; Hallett, J. P. Structural changes in lignins isolated using an acidic ionic liquid water mixture. Green Chem., 2015, 17, 5019-5034.

Cao, Y. et al. "Advances in lignin valorization towards bio-based chemicals and fuels: lignin biorefinery" Bioresour Technol. 2019;291: 121878.

Chio, C. et al. "Lignin utilization: a review of lignin depolymerization from various aspects" Renew Sustain Energy Rev. 2019;107:232-49.

Crestini, C. et al. "On the structure of softwood kraft lignin" Green Chem. 2017;19(17):4104-21.

Curia, S. et al. "Towards sustainable high-performance thermoplastics: synthesis, characterization, and enzymatic hydrolysis of bisguaiacol-based polyesters" Chemsuschem. 2018;11(15):2529-39.

Das, A. et al. "Lignin conversion to low-molecular-weight aromatics via an aerobic oxidation-hydrolysis sequence: comparison of different lignin sources" ACS Sustain Chem Eng. 2018;6(3):3367-74.

Davis, R, et al. "Process design and economics for the conversion of lignocellulosic biomass to hydrocarbons: dilute-acid and enzymatic deconstruction of biomass to sugars and catalytic conversion of sugars to hydrocarbons" Golden: National Renewable Energy Laboratory; 2015.

Dessbesell, L. "Bio-based polymers production in a kraft lignin biorefinery: techno-economic assessment" Biofuels Bioprod Bioref. (2017) 12:239-50.

Fache, M. et al. "Vanillin production from lignin and its use as a renewable chemical" ACS Sustain Chem Eng. (2016) 4(1):35-46.

Gould et al. "Alkaline Peroxide Delignification of Agricultural Residues to Enhance Enzymatic Saccharification" Biotechnology and Bioengineering, 1984, 46-52.

Gould, J. M. et al. "High-Efficiency Ethanol Production from Lignocellulosic Residues Pretreated with Alkaline H2O2" Biotechnol Bioeng 1984, 26:628-631.

Gould, J. M. "Studies on the Mechanism of Alkaline Peroxide Delignification of Agricultural Residues" Biotechnol Bioeng 1985, 27:225-231.

Gueneau et al. "Pulp delignification with oxygen and copper(II)-polyimine complexes" Holzforschung, 2014, 68(4), 377-384, published online Dec. 11, 2013.

Hakola "Liberation of Cellulose from the Lignin Cage: A Catalytic Pretreatment Method for the Production of Cellulosic Ethanol" ChemSusChem 2010, 3, 1142-1145.

Hambleton, K.M. and Stanzione, J.F. III. "Synthesis and characterization of a lowmolecular-weight novolac epoxy derived from lignin-inspired phenolics" ACS Omega (2021) 6(37): 23855-61.

Hocking, M.B. "Vanillin: synthetic flavoring from spent sulfite liquor" J Chem Educ. (1997) 74:1055-9.

Humbird, D. et al. "Process design and economics for biochemical conversion of lignocellulosic biomass to ethanol: dilute-acid pretreatment and enzymatic hydrolysis of corn stover" (2011) United States: National Renewable Energy Laboratory.

James, R.E. et al. "Cost and performance baseline for fossil energy plants vol. 1: bituminous coal and natural gas to electricity" SSRN J. (2019) https://doi.org/10.2139/ssrn.33659 92.

Ji, Y. et al. "New kinetics and mechanisms of oxygen delignification observed in a continuous stirred tank reactor" Holzforschung (2009) 63(3), 264-271.

Ji, Y. et al. "Oxygen delignification kinetics: CSTR and batch reactor comparison" AIChE J. (2007) 53(10), 2681.

Kerley, M. S., Fahey Jr, G. C., Berger, L. L., Gould, J. M., & Baker, F. L. (1985). Alkaline hydrogen peroxide treatment unlocks energy in agricultural by-products. Science 230:820-822.

Krothapalli, D.K., Genco, J.M., van Heiningen, A. "Gas-liquid mass transfer in laboratory oxygen-delignification reactors." 2006. J Pulp Paper Sci. 32(2), 53-58.

Lancefield, C.S. et al. "Investigation of the chemocatalytic and biocatalytic valorization of a range of different lignin preparations: the importance of β-O-4 content" ACS Sustain Chem Eng. (2016) 4(12):6921-30.

Li, et al. "Catalysis with CuII(bpy) Improves Alkaline Hydrogen Peroxide Pretreatment" Biotechnol Bioeng. 110(4):1078-1086 (2013).

Li, et al. "Rapid and Effective Oxidative Pretreatment of Woody Biomass at Mild Reaction Conditions and Low Oxidant Loadings" Biotechnol Biofuels 6(1), 119 (2013).

Liu, Y. et al. "Assessing the specific energy consumption and physical properties of comminuted Douglas-fir chips for bioconversion" Ind Crops Prod. (2016) 94:394-400.

(56) References Cited

OTHER PUBLICATIONS

Liu, et al., "Coupling alkaline pre-extraction with alkaline-oxidative post-treatment of corn stover to enhance enzymatic hydrolysis and fermentability" Biotechnology for Biofuels, 2014, 7:48.

Ou, L. et al. "Impacts of feedstock properties on the process economics of fast-pyrolysis biorefineries" Biofuels Bioprod Biorefin. 2018;12(3):442-52.

Pinales-Marquez, C.D. et al. "Circular bioeconomy and integrated biorefinery in the production of xylooligosaccharides from lignocellulosic biomass: a review" Ind Crops Prod. (2021) 162: 113274.

Ragauskas, A.J. et al. "Lignin valorization: improving lignin processing in the biorefinery" Science. 2014;344(6185):1246843.

Rahimi et al. "Chemoselective Metal-Free Aerobic Alcohol Oxidation in Lignin" 2013. J Am Chem Soc. 135, 6415.

Rahimi A, "Formic-acid-induced depolymerization of oxidized lignin to aromatics" Nature. 2014;515(7526):249-52.

Raud, M. et al. "Potentials and challenges in lignocellulosic biofuel production technology" Renew Sustain Energy Rev. 2019;111:44-56.

Rinaldi, R. et al. "Paving the way for lignin valorisation: recent advances in bioengineering, biorefining and catalysis" Angew Chem Int Ed. 2016;55(29):8164-215.

Sadler, J.C. and Wallace, S. "Microbial synthesis of vanillin from waste poly (ethylene terephthalate)" Green Chem. 2021;23(13):4665-72.

Sannigrahi, P. et al. "Pseudo-lignin and pretreatment chemistry" Energy Environ Sci. 2011;4(4):1306-10.

Schutyser, W. "Revisiting alkaline aerobic lignin oxidation" Green Chem. 2018;20(16):3828-44.

Singh, S.K. et al. "Integrated two-stage alkaline-oxidative pretreatment of hybrid poplar. Part 1: impact of alkaline pre-extraction conditions on process performance and lignin properties" Ind Eng Chem Res. 2019;58(35):15989-99.

Soltanian, S. et al. "A critical review of the effects of pretreatment methods on the exergetic aspects of lignocellulosic biofuels" Energy Conver Manag. 2020;212: 112792.

Sudarsanam, P. et al. "Recent developments in selective catalytic conversion of lignin into aromatics and their derivatives" Biomass Convers Biorefin. 2019;10:873-83.

Tan, ECD, et al. "Direct production of gasoline and diesel fuels from biomass via integrated hydropyrolysis and hydroconversion process—a techno-economic analysis" Environ Prog Sus Energ. 2013;33:609-17.

* cited by examiner

ECONOMICAL METHODS FOR PERFORMING OXIDATIVE CATALYTIC PRETREATMENT OF PLANT BIOMASS USING A SINGLE-STAGE TWO OXIDANT PROCESS

STATEMENT OF GOVERNMENT RIGHTS

This invention was made with government support under Funding Opportunity Announcement Numbers DE-EE0008148 and DE-SC0018409 awarded by the U.S. Department of Energy, Office of Energy Efficiency and Renewable Energy. The government has certain rights in the invention.

BACKGROUND

Cellulosic biofuels offer enormous potential as sustainable, low-carbon alternative liquid transportation fuels to petroleum-derived fuels. The vast majority of carbon in the terrestrial biosphere is contained in the cell walls of plants or lignocellulose. This enormous reservoir of reduced carbon is largely untapped for conversion to fuels, chemicals, and polymers as consequence of the difficulty in deconstructing the biopolymers contained in the plant cell wall matrix to a suite of chemicals that are amenable to conversion processes.

SUMMARY

Concerns over energy security and climate change have resulted in considerable effort focused on facilitating the transition of the fossil fuel-based economy to a renewable resource-based sustainable economy. Among the renewable resources currently available, lignocellulosic biomass is an abundant, potentially carbon-neutral source and is a promising raw material to produce biofuels and biomaterials at large scales. The challenge of developing efficient lignocellulosic biorefineries, however, is the high recalcitrance and complex structure of the plant cell walls which hinders both bioconversion and chemical conversion processes. Thus, a pretreatment technology that can economically fractionate lignocellulosic biomass into renewable biopolymers is highly desirable. The fractionated polysaccharides can be converted into monomeric sugars and biofuels, while lignin can be used as the starting material to produce various chemicals, materials, and fuels. Thus, an effective pretreatment approach that simultaneously maximizes polysaccharide hydrolysis to fermentable sugars and extracts high-quality lignin for subsequent valorization would improve the economic viability of the lignocellulosic-to-biofuel industry.

A sequential two-stage pretreatment process includes an alkaline pre-extraction stage followed by an alkaline oxidative pretreatment process with a metal-ligand homogenous catalyst (two-stage/one oxidant process). This process is described in U.S. patent application Ser. No. 16/206,848, incorporated herein by reference in its entirety. A challenge associated with this two-stage alkaline pre-extraction/Cu-catalyzed alkaline hydrogen peroxide (Cu-AHP) pretreatment process as well as other oxidative pretreatment processes is the process economics, especially the cost of the hydrogen peroxide ($H_2O_2$). To improve the economics of this oxidative lignocellulosic-to-biofuel technique, a reduction in the loading of expensive chemical inputs in conjunction with an increase in the recovery of biomass polymers is advantageous.

Employing $O_2$, e.g., at about 50 psi, in addition to $H_2O_2$ as a co-oxidant during a two-stage alkaline pre-extraction/copper 2,2'-bipyridine catalyzed alkaline hydrogen peroxide (Cu-AHP/O) pretreatment process resulted in a substantial improvement in delignification relative to using $H_2O_2$ alone during the second stage of the Cu-AHP/O pretreatment, leading to high overall sugar yields even at $H_2O_2$ loadings as low as 2% (w/w of original biomass). This two-stage, two oxidant process is described in U.S. patent application Ser. No. 16/903,598, incorporated herein by reference in its entirety. The two stage/two oxidant pretreatment process while employing oxygen will be referred to herein as Cu-AHP/O process. Performing analogous reactions in the absence of $H_2O_2$ (with only addition of oxygen) resulted in approximately 25% less delignification and a 30% decrease in overall sugar yields. The isolated lignin from this dual oxidant process had high aliphatic hydroxyl group content and reactivity to isocyanate, indicating that it is a promising substrate to produce polyurethanes. To test the suitability of the isolated lignin as a source of aromatic monomers, the lignin was subjected to a sequential Bobbitt's salt oxidation followed by formic-acid catalyzed depolymerization process. Monomer yields of approximately 17% were obtained, and the difference in yields was not significant between lignin isolated from the Cu-AHP process with and without $O_2$ as a co-oxidant, suggesting that the addition of $O_2$ did not lead to significant lignin crosslinking. Technoeconomic analysis (TEA) indicates that using both $O_2$ and $H_2O_2$ as co-oxidants for the Cu-AHP/O alkaline oxidative pretreatment process could potentially reduce the minimum biofuel selling price (MFSP) to as low as $0.77/L, 40% lower than using $H_2O_2$ only.

The present description includes a process for improving the economics by utilizing a single stage/two oxidant process. The single stage process eliminates the alkaline pre-extraction stage prior to the alkaline oxidative pretreatment stage and surprisingly can generate results comparable to a two stage-two oxidant process. This can be advantageous as it streamlines the process, reduces the costs, and improves MFSP while maintaining and/or improving the lignin and sugar yields from the process. The single stage process can combine the alkaline pre-extraction step and the alkaline oxidative pretreatment process with a metal-ligand homogenous catalyst with at least two oxidants into a single step process. (See FIG. 1A and FIG. 1B) In one embodiment, the co-oxidant can partially substitute for the $H_2O_2$ while maintaining or increasing monomer sugar yields and lignin solubilization. The present description describes using pressurized $O_2$ as a co-oxidant along with $H_2O_2$ during a single-stage alkaline Cu-AHP/O pretreatment process to improve the recovery of biopolymers, including both polysaccharides and lignin. This process will be referred to herein as single-stage-AHP/O or ss-AHP/O or ss-Cu-AHP/O process. The results indicate that the inclusion of enhanced amounts of $O_2$ as a co-oxidant in a single stage surprisingly led to comparable or enhanced lignin solubilization, a lower chemical input requirement, improved or comparable total sugar release by enzymatic hydrolysis, and reduced processing costs. In one embodiment, the ss-AHP/O produced comparable results to the two stage, two-oxidant (Cu-AHP/O) process. Moreover, the properties of the lignin isolated from this process (high hydroxyl content, >6.5 mmol/g) indicate that it could be an excellent renewable polyol in the formulation of lignin-based polyurethanes. Furthermore, the susceptibility of the lignin towards oxidative depolymerization suggests that the use of enhanced levels of $O_2$ as a co-oxidant did not result in the formation of additional lignin crosslinks, and the lignin remains amenable to valorization via depolymerization into monomers. Technoeconomic analysis (TEA) suggests that minimum fuel selling price (MFSP) of the ss-AHP/O pretreatment could be reduced by as much as 40% relative to using a two-stage Cu-AHP/O. Together, these results highlight the utility of using a single-stage alkaline oxidative pretreatment with enhanced levels of $O_2$ as an inexpensive and environmentally friendly co-oxidant in conjunction with $H_2O_2$ during metal-catalyzed alkaline oxidative pretreatments.

In the following detailed description, embodiments are described in sufficient detail to enable those skilled in the art to practice them, and it is to be understood that other embodiments may be used and that chemical and procedural changes may be made without departing from the spirit and scope of the present subject matter. The following detailed description is, therefore, not to be taken in a limiting sense, and the scope of embodiments of the present invention is defined only by the appended claims.

The various embodiments described herein provide a method of pretreating plant biomass comprising a single-stage pretreatment of plant biomass, wherein the single-stage pretreatment includes catalytically pretreating the plant biomass with a metal-ligand complex and at least two oxidants in an alkaline oxidative pretreatment process to produce a catalytically pretreated plant biomass. In one embodiment, the oxidants are oxygen and hydrogen peroxide. In one embodiment, the oxygen pressure is from about 100 psi to about 500 psi and the hydrogen peroxide is less than about 8% (w/w of original biomass), for example, between about 2% and about 8%. In one embodiment, at least two oxidants are present simultaneously in the pretreatment.

In one aspect, the present description relates to a method of pretreating plant biomass. The method includes catalytically pretreating the plant biomass in a single-stage alkaline oxidative pretreatment process, wherein the process includes providing a metal-ligand complex, providing a base, and adding at least two oxidants to the alkaline oxidative pretreatment process to produce a catalytically pretreated plant biomass. The method does not include an alkaline pre-extraction step prior to the alkaline oxidative pretreatment process. The method may include pressurized oxygen and hydrogen peroxide as the oxidants. The method may include oxygen pressure from 100 psi to about 400 psi and hydrogen peroxide at less than about 6% (w/w). The method may include the two oxidants present simultaneously in the pretreatment. The method may include the alkaline oxidative pretreatment conducted at a temperature from about 70° C. to about 140° C. The method may further include addition from about 5% to about 15% sodium hydroxide (w/w) to the alkaline oxidative pretreatment process. The method may include a metal-ligand complex having a second ligand.

The method may include a catalytic pretreating step that produces a liquid phase and the method further including separating the catalytically pretreated biomass from the liquid phase to produce separated catalytically pretreated biomass and hydrolyzing the separated catalytically pretreated biomass to produce hydrolyzed catalytically pretreated biomass. The method may include conducted the hydrolyzing with an enzyme, wherein the enzyme is at a concentration from about 5 mg protein/g glucan to about 30 mg protein/g glucan.

In another aspect, the present description relates to a method of reducing cost in a homogenous catalytic reaction. The method includes catalytically pretreating plant biomass with a metal-ligand complex and at least two oxidants present in a single-stage alkaline oxidative pretreatment process to produce a catalytically pretreated plant biomass and hydrolyzing the catalytically pretreated biomass to produce hydrolyzed catalytically pretreated biomass for use as a biofuel. The method does not include an alkaline pretreatment step prior to the alkaline oxidative pretreatment step. The method may include pressurized oxygen and hydrogen peroxide as the oxidants. The method may include oxygen pressure from 100 psi to about 400 psi and hydrogen peroxide at less than about 6% (w/w). The method may include the two oxidants present simultaneously in the pretreatment. The method may include the alkaline oxidative pretreatment conducted at a temperature from about 70° C. to about 140° C. The method may further include addition from about 5% to about 15% sodium hydroxide (w/w) to the alkaline oxidative pretreatment process. The method may include a metal-ligand complex having a second ligand.

The method may include a catalytic pretreating step that produces a liquid phase and the method further including separating the catalytically pretreated biomass from the liquid phase to produce separated catalytically pretreated biomass and hydrolyzing the separated catalytically pretreated biomass to produce hydrolyzed catalytically pretreated biomass. The method may include conducted the hydrolyzing with an enzyme, wherein the enzyme is at a concentration from about 5 mg protein/g glucan to about 30 mg protein/g glucan. The method may reduce the minimum fuel selling price (MFSP) by about 40% relative to the MFSP of a method using only hydrogen peroxide as the oxidant.

In yet another aspect, the present description relates to a method of pretreating plant biomass. The method includes catalytically pretreating the plant biomass in a single-stage alkaline oxidative pretreatment process, wherein the process comprises providing a metal-ligand complex and adding at least two oxidants to the alkaline oxidative pretreatment process to produce a catalytically pretreated plant biomass and wherein the one of at least two oxidants comprises pressurized oxygen at least 100 psi. The method may include hydrogen peroxide as one of the oxidants. The method may include pressurized oxygen from 100 psi to about 400 psi and the hydrogen peroxide at less than about 6% (w/w). The method may include the two oxidants present simultaneously in the pretreatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figures 1A, 1B:
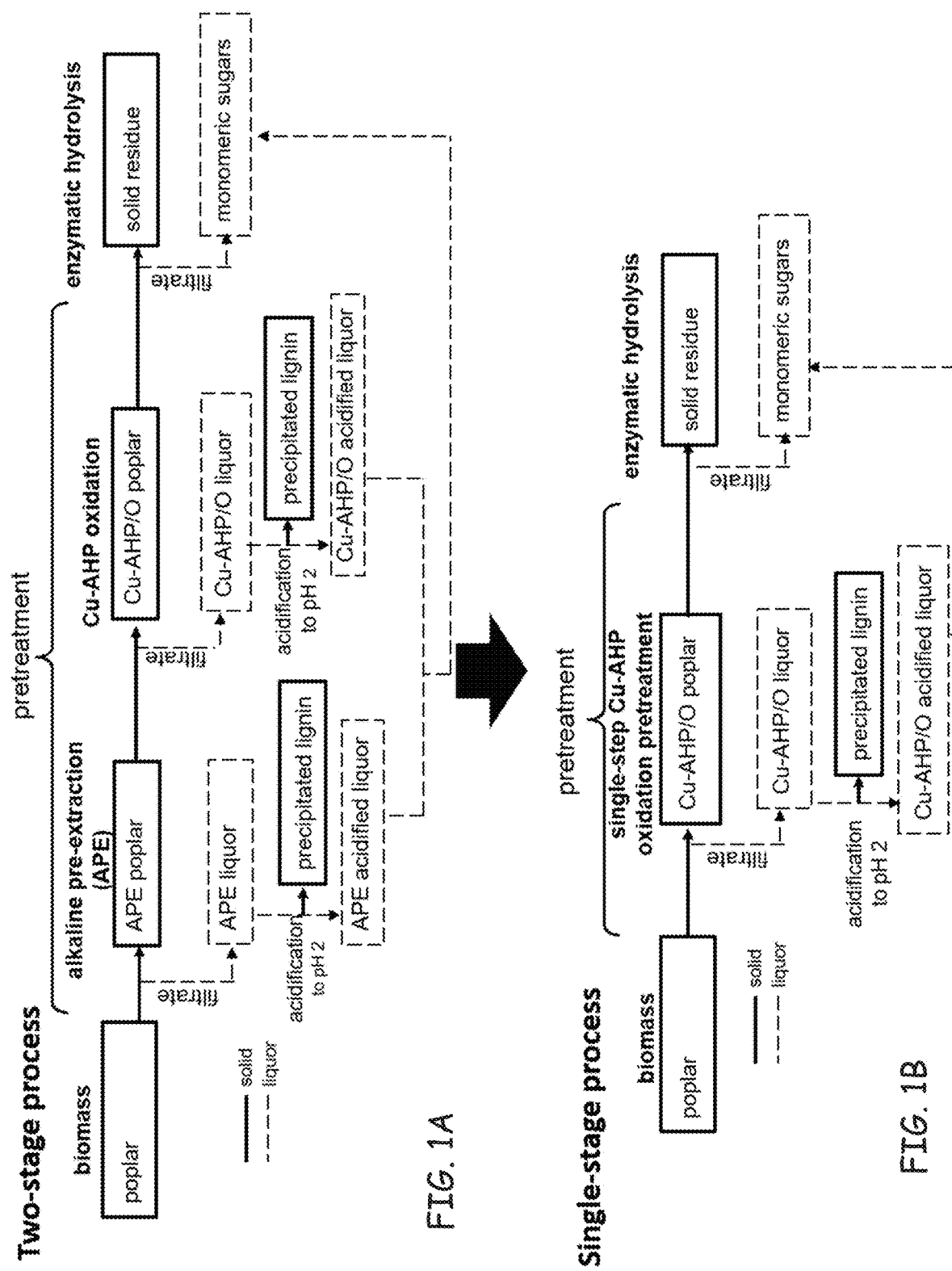
FIG. 1A is a schematic of a prior two-stage process of alkaline oxidative pretreatment for pretreatment of plant biomass.
FIG. 1B is a schematic of a single-stage alkaline oxidative pretreatment process described herein for pretreatment of plant biomass.

In the following detailed description, embodiments are described in sufficient detail to enable those skilled in the art to practice them, and it is to be understood that other embodiments may be used and that chemical and procedural changes may be made without departing from the spirit and scope of the present subject matter. The following detailed description is, therefore, not to be taken in a limiting sense, and the scope of embodiments of the present invention is defined only by the appended claims.

The term "biomass" as used herein, refers in general to organic matter harvested or collected from a renewable biological resource as a source of energy and bioproducts. The renewable biological resource can include plant materials, animal materials, and/or materials produced biologically. The term "biomass" is not considered to include fossil fuels, which are not renewable.

The term "plant biomass" or "ligno-cellulosic biomass (LCB)" as used herein is intended to refer to any plant-derived organic matter containing cellulose and/or hemicellulose as its primary carbohydrates (woody or non-woody) available for producing energy on a renewable basis and bioproducts. Plant biomass can include, but is not limited to, agricultural residues such as corn stover, wheat straw, rice straw, sugar cane bagasse, sorghum, and the like. Plant biomass can also include agricultural residues and forest residues that are dedicated for bioenergy purposes, such as residues of grasses and trees. Plant biomass further includes, but is not limited to, "woody biomass", i.e., woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally, perennial grass crops, such as various prairie grasses, including prairie cord grass, switchgrass, *Miscanthus*, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States. When describing the various embodiments and used without a qualifier, the term "biomass" is intended to refer to "plant biomass," i.e., lignocellulosic biomass (LCB) containing plant cell wall polysaccharides.

The term "biofuel" as used herein, refers to any renewable solid, liquid, or gaseous fuel produced biologically and/or chemically, for example, those derived from biomass. Most biofuels are originally derived from biological processes such as the photosynthesis process and can therefore be considered a solar or chemical energy source. Some types of biofuels, such as some types of biodiesel, can be derived from animal fats. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal solid waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops, lignocellulosic crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg, and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "pretreatment step" as used herein, refers to any step intended to alter biomass so it can be more efficiently and economically converted to reactive intermediate chemical compounds such as sugars, organic acids, etc., which can then be further processed to a variety of end products such as ethanol, isobutanol, long chain alkanes, etc. Pretreatment can reduce the degree of crystallinity of a polymeric substrate, reduce the interference of lignin with biomass conversion, and hydrolyze some of the structural carbohydrates, thus increasing their enzymatic digestibility and accelerating the degradation of biomass to useful products. Pretreatment methods can utilize acids of varying concentrations, including dilute acid pretreatments, concentrated acid pretreatments (using, for example, sulfuric acids, hydrochloric acids, organic acids, and the like) and/or pretreatments with alkali such as ammonia and/or ammonium hydroxide and/or calcium hydroxide and/or sodium hydroxide and/or lime, and the like, and/or oxidative pretreatments using oxidants such as air, oxygen, hydrogen peroxide, organic peroxide, ozone, and the like.

Pretreatment methods can additionally or alternatively utilize hydrothermal treatments including water, heat, steam, or pressurized steam pretreatments, including, but not limited to, hydro-thermolysis pretreatment and liquid hot water pretreatment, further including, for example, acid catalyzed steam explosion pretreatment (e.g., $SO_2$ catalyzed). Pretreatment can occur or be deployed in various types of containers, reactors (e.g., batch, counter-current, and the like), pipes, flow through cells, and the like. Many pretreatment methods will cause the partial or full solubilization and/or destabilization of lignin and/or hydrolysis of hemicellulose to pentose sugars. Further examples of pretreatment include, but are not limited wet oxidation, organosolv pretreatment and mechanical extrusion.

The term "metal-ligand complex" as used herein refers to a metal complex containing one or more metal-coordinating ligands and one or more metal atoms which are in a state of interaction with each other. Such interactions include various types of forces and bonds, which include, but are not limited to, ionic bonds, covalent bonds, and van der Waals forces. The term "metal-ligand complex" and "ligand-metal complex" can be used interchangeably.

The term "metal-coordinating ligand" as used herein refers to a ligand, such as an ion, a molecule, or the like, that can interact with the metal portion of a metal-ligand complex. When used without qualification, the term "ligand" is intended to refer to a "metal-coordinating ligand."

The term "copper-coordinating ligand" as used herein refers to a metal coordinating ligand capable of interacting with copper atoms or copper ions.

The term "single-ligand metal complex" as used herein refers to a metal-ligand complex containing only one ligand that coordinates with, i.e., interacts with metal atoms or metal ions.

The term "multi-ligand metal complex" as used herein refers to a metal-ligand complex containing more than one ligand that coordinates with, i.e., interacts with metal atom or metal ions.

The term "toxicity" as used herein refers to ions, molecules, and metal-ligand complexes present in the process streams during biomass conversion and cellulosic biofuel production that negatively impact the yield of the products.

The term "slow add" as used herein refers to a gradual rate of addition of a reagent to a reaction vessel. The gradual rate can be continuous or discontinuous, i.e., it may include intermittent periods of no reagent being added. A "slow add" is in contrast to a batch method of adding a reagent, in which all the desired reagent is added to the reactive vessel at once.

The term "state of interaction" as used herein refers to an interaction between a ligand and a metal or between a metal and multiple ligands. Such an interaction can include various types of forces and bonds, which include, but are not limited to, ionic bonds, covalent bonds, and van der Waals forces.

The term "alkaline oxidative pretreatment" as used herein relates to a pretreatment of plant biomass in an alkaline environment with one or more oxidants. which can include, but are not limited to, hydrogen peroxide, oxygen, ozone, hydroperoxide anion, superoxide radical, hydroxyl radical, and peroxy acids (e.g., peracetic acid, peroxymonosulfuric acid, peroxyphosphoric acid, and meta-chloroperoxybenzoic acid). See, for example, Liu, et al., *Coupling alkaline pre-extraction with alkaline-oxidative post-treatment of corn stover to enhance enzymatic hydrolysis and fermentability*, Biotechnology for Biofuels, 2014, 7:48, which describes example conditions for alkaline oxidative pretreatment. An alkaline oxidative pretreatment which uses hydrogen peroxide as one of the oxidants is to be distinguished from a conventional "alkaline hydrogen peroxide" (AHP) pretreatment which is a one-step catalytic pretreatment process which requires much higher oxidant loadings. See, for example, Biotechnol Bioeng 1984, 26:46-52; Biotechnol Bioeng 1984, 26:628-631; Biotechnol Bioeng 1985, 27:225-231; Science 1985, 230:820-822 and Biotechnol Biofuels 2011, 4:16, which describe conventional AHP with much higher oxidant loadings.

The term "ss-AHP/O" process, "ss-Cu-AHP/O" process or "ss-dual oxidant" process as used herein relates to a single-stage alkaline oxidative pretreatment with at least two oxidants. The terms may be used interchangeably. While the present description is in the context of hydrogen peroxide and oxygen as the two oxidants, it will be understood that other oxidants may also be used in the oxidative treatment.

Nearly all forms of lignocellulosic biomass, i.e., plant biomass, such as monocots, comprise three primary chemical fractions: hemicellulose, cellulose, and lignin. Lignin, which is a polymer of phenolic molecules, provides structural integrity to plants, and is difficult to hydrolyze. As such, after sugars in the biomass have been fermented to a bioproduct, such as alcohol, lignin remains as residual material, i.e., a non-easily digestible portion.

Cellulosic biofuel production from lignocellulosic biomass has gained considerable momentum due to both environmental and social sustainability benefits. However, the technology is not yet fully commercialized. One issue impeding cellulosic biofuel production using the sugar platform is the hydrolysis-resistant nature of certain components in the lignocellulosic biomass.

Cellulose and hemicelluloses in plant cell walls exist in complex structures within the residual material. Hemicellulose is a polymer of short, highly branched chains of mostly five-carbon pentose sugars (xylose and arabinose), and to a lesser extent six-carbon hexose sugars (galactose, glucose and mannose). Because of its branched structure, hemicellulose is amorphous and relatively easy to hydrolyze into its individual constituent sugars by enzyme or dilute acid treatment. Cellulose is a linear polymer comprising of $\beta(1,4)$ linked D-glucose in plant cell wall, much like starch with a linear/branched polymer comprising of $\alpha(1,4)$ linked D-glucose, which is the primary substrate of corn grain in dry grind and wet mill ethanol plants. However, unlike starch, the glucose sugars of cellulose are strung together by β-glycosidic linkages, which allow cellulose to form closely associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Although hemicellulose sugars represent the "low-hanging" fruit for conversion to a biofuel, the substantially higher content of cellulose represents the greater potential for maximizing biofuel yields, on a per ton basis of plant biomass.

Lignocellulose can also be characterized as a highly heterogeneous composite material comprised of multiple cell wall biopolymers (cellulose, heteropolysaccharides including hemicelluloses and pectins, and lignins) associated primarily by non-covalent interactions which are assembled into cell walls with composition and properties varying by cell and tissue type. These components are interconnected through a variety of covalent and non-covalent interactions, giving rise to a highly organized network which is assembled in a tightly controlled sequence during plant growth. This heterogeneous higher order structure of the cell wall impacts the cell wall's response to deconstruction and conversion.

Plant cell walls exhibit substantial heterogeneity in both content and distribution of the inorganic elements which also have implications for biomass conversion processes. This includes differences between content and distribution of inorganics in disparate plant taxa, differences between related species, within a single species as a function of its phenotype and environment, and even between tissues in a single plant.

Inorganic elements in plants are known to be responsible for diverse roles, including maintenance of ionic equilibrium in cells (e.g., K) and storage (e.g., Fe in ferritin), which, despite being localized in plastids, is water extractable. A subset of the inorganic elements in plants is strongly associated with the cell wall. These elements are more resistant to aqueous extraction and include inorganic elements that may have structural roles, including, but not limited to, Ca and B ionic cross-links in pectic polysaccharides, calcium oxalate raphide crystals in some grasses, and Si in the cell walls of grasses which can comprise a significant fraction of the mass of a plant. Another class of role of cell-wall associated inorganic elements are metal co-factors in enzymes (e.g., Zn, Fe, Mn, Cu).

Redox-active metals, such as Cu, Mn, Fe, can exist in multiple oxidation states in vivo and are often involved in reactions involving electron transfer. Specifically, Fe in plants is associated with Fe-heme proteins and iron-sulfur (Fe—S) clusters in proteins, such as ferredoxins, which function as electron carriers in the photosynthetic electron transport chain. Cu in plants has diverse roles as a structural element in regulatory proteins, in photosynthetic electron transport, mitochondrial respiration, and Fe mobilization, among others. Metals may also be associated with metallothioneins (MTs) and phytochelatins (PCs), which are cysteine-rich polypeptides involved in either ameliorating the toxicity or controlling homeostasis of metals such as Fe, Ni, Cd, Zn, and Cu by coordination by thiols. In addition to its involvement with enzymes associated with the shikimic acid pathway and lignin biosynthesis, Mn is contained in a metallo-oxo cluster containing 4 Mn ions at differing oxidation states in the oxygen-evolving complex of photosystem II.

There are differences in the strength and nature of association of cell wall-associated metals. Specifically, Mn may be strongly associated with the cell wall and be present in "organic chelates" or "bound to lignin." Alkali delignified hardwoods are known to have differences in the extractability of cell wall-associated Mn versus Fe using chelating compounds. Mg, which is a component of chlorophyll, is useful for photosynthesis and protein synthesis, although a portion of Mg may be bound to pectin or precipitated as salts in the vacuole, while the remainder is extractable with water.

During either oxidative delignification or biomass conversion processes where oxygen may be present, cell wall-associated transition metals can catalyze the formation of reactive oxygen species through Fenton chemistry. This catalytic activation of oxygen by transition metals has been shown to contribute to the oxidative scission of polysaccharides during alkaline-oxidative bleaching or delignification using $H_2O_2$ or $O_2$. As a result, precautions are taken during these processes through chelation and washing steps to remove metals and addition Mg salts and silicates to complex transition metals during these unit operations.

Therefore, a pretreatment process is typically used to alter and expand the cell wall matrix, to hydrolyze the hemicelluloses, and to alter the hemicelluloses. Pretreatment disrupts the non-easily digestible portion of lignocellulosic biomass, e.g., cellulose and lignin, thus improving its accessibility. After pretreatment, much of the biomass becomes easily digestible, while a portion remains non-easily digestible. Ultimately, the pretreatment process makes the cellulose more accessible (during a subsequent hydrolysis process, such as with lytic enzymes) for conversion of the lignocellulose polysaccharides (e.g., cellulose and hemicellulose) to monomeric sugars, which can be transformed to target products via catalytic conversion or microbial fermentation.

However, enzymatic hydrolysis of lignocellulose polysaccharides is usually hindered by the natural resistance of plant cell wall against deconstruction. To overcome this resistance, pretreatment processes of biomass feedstock have been developed and employed. Biomass pretreatment modifies cell wall structure and renders the biomass more digestible by enzymes.

A wide range of pretreatments are known, but few pretreatment methods have been identified as effective for biomass feedstocks, such as woody biomass, which are highly resistant to enzymatic hydrolysis. For example, enzymatic hydrolysis of hybrid poplar wood usually produces sugars at only 5 to 30% of the theoretical maximum yield. As noted above, such resistance involves the structural rigidity of the plant cell wall, the crystallinity of cellulose, and the presence of lignin, which remains as a residual material.

However, in the embodiments described herein, the alkaline pretreatments not only solubilize the lignin, it is expected that they also produce a lignin that closely resemble native lignin, such that less than 35% of the α-carbon of the solubilized lignin is oxidized from a hydroxyl to a carbonyl.

Lignin is known to be useful in a variety of applications including, but not limited to, carbon fiber composites, bio-oil, resins, adhesive binders and coating, plastics, paints, enriching soil organic carbon, fertilizer, rubbers and elastomers, paints, antimicrobial agents, and slow nitrogen release fertilizer, and the like, and can be a substitute for polymers produced using crude oil.

One current source of lignin in the market is produced from sulfite (or sulfonate) based paper/pulp mills, a kraft pulping process, and the like. Most such mills currently burn the lignin to recover energy and to reduce the environmental impact of discharge. Very few sulfite mills currently process the lignosulfonates from sulfite spent liquors. Additionally, the quality and quantity of lignin obtained via currently known methods are inadequate for most applications. As such, methods to fractionate and convert lignin into value-added products are needed.

Known methods for pretreating plant biomass are typically performed under elevated pressures and temperatures (above room temperature). Such methods include hot water and steam treatments, ammonia treatments and sulfite treatments.

Other pretreatment methods utilize an oxidant-based pretreatment, such as the alkaline oxidative pretreatment (AOP) process or a conventional alkaline hydrogen peroxide known by those skilled in the art. Yet other methods include catalytic processes. Catalytic approaches to plant cell wall deconstruction and conversion of insoluble biomass rely on homogeneous catalysts to allow the catalyst to diffuse through nano-scale pores within the cell walls to perform the desired reactions. Heterogeneous catalysis is known to be inefficient unless the cell walls are solubilized in expensive solvents such as ionic liquids. Homogeneous catalysts are used in many applications, such as homogeneous copper catalysts used for atom transfer radical polymerization where catalyst removal to prevent contamination of the product adds cost to the process.

Table 1 (below) summarizes some known pretreatment methods and the pretreatment method described herein.

second stage with another addition of 10% NaOH, about 2% hydrogen peroxide and about 50 psi of oxygen.

In various embodiments, a single-stage, alkaline oxidative pretreatment process with two or more oxidants is described herein (ss-dual oxidant process). In one embodiment, the single stage alkaline oxidative pretreatment process with two oxidants can be a single stage $O_2$-enhanced alkaline

TABLE 1

| | Name | Pre-extraction Base amount | Pretreatment | Temp. | Other cond. | Reference |
|---|---|---|---|---|---|---|
| Single stage catalytic pretreatment process | Reference-Cu-AHP process (AOP) | None | 10% $H_2O_2$ | R.T. | 2 mM 2,2'-bipyridine, 1 mM $CuSO_4$ | Li, Z., Chen, C. H., Hegg, E. L., & Hodge, D. B. (2013). Biotechnology for Biofuels, 6, 119. |
| Two stage One oxidant, Metal-single ligand catalyst | Cu-AHP process | 10% NaOH | 10% $H_2O_2$, | R.T. | 2 mM 2,2'-bipyridine, 1 mM $CuSO_4$ | Bhalla, A., Bansal, N., Stoklosa, R. J., Fountain, M., Ralph, J., Hodge, D. B., & Hegg, E. L. (2016). Biotechnology for biofuels, 9(1), 1-10. |
| Two stage 2 oxidant | Cu-AHP/O process | 10% NaOH, 120° C. | $H_2O_2$ (2-10%) $O_2$ (25-50 psi) 10% NaOH, 80° C. | 120° C. pre-extraction and 80° C. oxidative post treatment | 1 mM 2,2'-bipyridine, 1 mM $CuSO_4$ | Yuan, Z., Klinger, G. E., Nikafshar, S., Cui, Y., Fang, Z., Alherech, M., . . . & Hegg, E. L. (2021). ACS Sustainable Chemistry & Engineering, 9(3), 1118-1127. |
| Single-stage 2 oxidant | ss-Cu-AHP/O) | None | $H_2O_2$ (2-10%) $O_2$ (100-300 psi) 15% NaOH | 80-100° C. | 1 mM 2,2'-bipyridine, 1 mM $CuSO_4$ | (described herein) |

Use of a single ligand copper complex as a catalyst in combination with an alkaline oxidative pretreatment (AOP) process with one oxidant is known. See, for example, Li et al., *Rapid and Effective Oxidative Pretreatment of Woody Biomass at Mild Reaction Conditions and Low Oxidant Loadings* Biotechnol Biofuels 6(1), 119 (2013), and Li, et al., Catalysis with $Cu^{II}$(bpy) Improves Alkaline Hydrogen Peroxide Pretreatment. Biotechnol Bioeng. 110(4):1078-1086 (2013), each of which is incorporated by reference in its entirety. However, the amount of oxidant required in such processes is high, such as at least 10% of the weight of the biomass to be treated. Additionally, to achieve suitable pretreatment results, the amount of metal utilized in a single-ligand copper complex is high (e.g., more than 50 μmol of metal complexes per gram of biomass to be pretreated). Use of such high levels of a metal can pose toxicity issues in subsequent processes (e.g., fermentation). Moreover, use of such high amounts of metals and oxidants can be cost prohibitive.

A sequential two-stage, dual oxidant pretreatment process has been described, for example, in U.S. patent application Ser. No. 16/903,598. In the two-stage pretreatment process as shown in FIG. 1A, the plant biomass is treated with alkaline, e.g., 10% NaOH in the first stage. The alkaline treated plant biomass is filtered and then the solids are subject to a second stage of pretreatment with two oxidants, e.g., pressurized oxygen and hydrogen peroxide, in an alkaline environment. The two stage, dual oxidant (Cu-AHP/O) process can include the use of about 10% NaOH in the first stage. After filtering, the solids are pretreated in the hydrogen peroxide (ss-Cu-AHP/O) pretreatment process that improves the economics of the oxidative lignocellulosic-to-biofuel technique. In one embodiment, the alkaline pre-extraction step prior to the addition of oxidants is eliminated resulting in a one-stage pretreatment process as shown in FIG. 1B. This process leads to a reduction in the loading of expensive chemical inputs in conjunction with an increase in the recovery of biomass polymers as well as significantly streamlining the process steps by elimination of the alkaline pre-extraction step. In one embodiment, the ss-dual oxidant process uses sodium hydroxide as the base, a metal-ligand complex, e.g., a copper-ligand complex, hydrogen peroxide in combination with pressurized oxygen as the oxidants. In one embodiment, a portion of the hydrogen peroxide generally used in a single oxidant process can be replaced with the molecular oxygen. Reduction of the hydrogen peroxide in the oxidative pretreatment process can lead to a cost savings. In one embodiment, in the dual oxidant process, the hydrogen peroxide and oxygen are present simultaneously in the oxidative pretreatment process.

In various embodiments, the ligand metal complexes with one or more ligands with two or more oxidants can be used in the single-stage alkaline oxidative pretreatment process of plant biomass.

In various embodiments, the ss-dual oxidant process described herein combines the alkaline pre-extraction first stage and the alkaline dual oxidant oxidative pretreatment second stage into a one-stage alkaline oxidative pretreatment process. In one embodiment, the present description includes a single-stage metal catalyzed alkaline oxidative pretreatment using two oxidants, e.g., both $O_2$ and $H_2O_2$, as co-oxidants to improve the enzymatic digestibility of the biomass as well as recovering high quality lignin to be converted into aromatic monomers such as vanillin, syringaldehyde, p-hydroxybenzoic, vanillic acid, and syringic acid. The ss-Cu-AHP/O process can improve the recovery of biopolymers, including both polysaccharides and lignin by eliminating the alkaline pre-extraction stage of the two-stage process. In one embodiment, the process described herein can increase the $O_2$ pressure and/or $H_2O_2$ loading during the alkaline oxidative pretreatment. This can eliminate the initial alkaline pre-extraction stage while maintaining high sugar yields and native-like lignin stream amenable to depolymerization into monomers or formulation of lignin-based polyurethanes. In one embodiment, this single stage strategy can utilize 25% less NaOH than a two-stage process and has the potential to improve the life cycle analysis (LCA) and simplify biomass handling and the entire plant biomass pretreatment process, thereby further reducing the minimum fuel selling price (MFSP).

In various embodiments, oxidants useful in an alkaline oxidative pretreatment process include, but are not limited to, air, oxygen, hydrogen peroxide, ozone, persulfate, percarbonate, sodium peroxide and combinations thereof. In one embodiment, the oxygen can be pressurized oxygen that is added or provided to the reaction in amounts greater than the amount of oxygen present in the atmospheric. In one embodiment, the process includes the addition of at least two oxidants to the reaction mixture containing the plant biomass for pretreatment.

In one embodiment, one or more oxidants are combined with the other reactants at a low weight percent (%) loading based on original biomass (w/w), i.e., loading of no more than 15% w/w based on original biomass. In one embodiment, the $H_2O_2$ loading is less than 10% w/w, such as less than 5% w/w based on original biomass. In one embodiment, the $H_2O_2$ loading ranges from about 1% to about 15%, such as about 1% to about 10%, such as about 1% to 5% or less, including any range there between based on original biomass w/w. Such loadings are lower than conventional $H_2O_2$ loadings which can be as high as 200%.

In various embodiments, the loading of hydrogen peroxide in the ss-AHP/O process can be less than about 10% w/w ($H_2O_2$/original biomass), or less than about 8% w/w, or less than about 5% w/w, or less than about 4% w/w, or less than about 3% w/w, or less than about 2% w/w, or less than about 1% w/w. In one embodiment, the loading of hydrogen peroxide in the ss-AHP/O process is about 2% w/w.

In various embodiments, the amount of oxygen used in the ss-AHP/O process is greater than about 50 psi, or greater than about 100 psi, or greater than about 250 psi, or greater than about 300 psi, or greater than about 400 psi. In various embodiments, the amount of oxygen used to enhance the ss-AHP/O process is less than about 500 psi, or less than about 400 psi, or less than about 350 psi, or less than about 300 psi. In one embodiment, the amount of oxygen used to enhance the ss-AHP/O process is about 300 psi.

In one embodiment, the oxidants used in the ss-AHP/O process included hydrogen peroxide at about 2% w/w and oxygen at about 300 psi. Variations of this combination of concentrations may be used as described above and are within the scope of this description.

In various embodiments, a single-ligand or a multi-ligand metal complex can be used in the ss-AHP/O process described herein. In one embodiment, a single-ligand metal complex may be used. In another embodiment, a multi-ligand metal complex may be used. In one embodiment, the metal-coordinating ligands includes 2,2'-bipyridine. Other metal-coordinating ligand, including, but not limited to nitrogen-donating ligands such as pyridine, 1,10-phenanthroline, and ethylenediamene, and ligands containing both a nitrogen donor and a carboxylate group such as the amino acids including histidine or glycine may also be used. In one embodiment, the catalytic metal element(s) (i.e., metal or metals) in the catalyst can include, but are not limited to, aluminum, zinc, nickel, magnesium, manganese, iron, copper cobalt and/or vanadium in various oxidation states. In various embodiments, the catalytic metal element is a metal ion(s). The metal ion(s) is redox active. The metal ions can be oxidized and/or reduced. In one embodiment, the elements include, but are not limited to, iron (e.g., Fe(II), Fe(III)), copper (e.g., Cu(I), Cu(II)), cobalt (e.g., Co(III), Co(VI)), and/or vanadium (e.g., V(II), V(III), V(IV), V(V)).

By substituting an amount of the 2,2'-bypyridine (bpy) with other, lower costs ligands, substantial savings can be achieved. In one embodiment, about 1 weight/weight (w/w) % up to about 99% or higher, such as 100% of bpy is substituted, such as about 10 to about 90%, such as about 20 to about 80%, such as about 35% to about 60%, including any range there between. In the various embodiments described herein, the multi-ligand metal complexes have low production costs. In one embodiment, substitution of bpy with other metal coordinating ligands provides a savings on the order of 10-fold or more, such as a savings of about 20 to 30 times the cost of using bpy alone.

In various embodiments, use of a multi-ligand metal complex in the ss-AHP/O process allows for a reduction in the amount of metals used in the process and also a reduction in the amount of oxidant. The multi-ligand metal complex can be, for example, a multi-ligand copper complex. The copper complex can be, for example, copper(II) 2,2'-bipyridine complex (Cu(bpy)) modified to contain at least one additional metal-coordinating ligand, such as pyridine; 1,10-phenanthroline; ethylenediamene; histidine; and/or glycine.

While not wishing to be bound by this proposed theory, both the single- and multi-ligand metal complexes are thought to function as suitable catalysts for lignocellulosic biomass (i.e., cause sufficient catalyst sorption into the biomass) due to the ability of the cationic metal, such as copper, to interact with (e.g., bond with) charged anionic groups, such as deprotonated phenolic hydroxyls in lignin, carboxylate groups in lignin, and/or uronic acids in pectins and hemicelluloses.

In one embodiment, use of the multi-ligand metal complex as a catalyst during an oxidative pretreatment may allow the pretreatment process to proceed significantly faster (e.g., at least two times as fast) as compared with an oxidative pretreatment performed using a conventional single-ligand metal complex as a catalyst.

In various embodiments, the ligand metal complexes can include any of the metals described herein. In one embodiment, the ligand metal complexes can be copper ligand complexes. The ligand can be any ligand as described herein. In various embodiments, the ligand metal complexes can include a single ligand. In various embodiments, the ligand metal complexes can be multi-ligand complexes as described herein. In one embodiment, the ligand metal complex is a Cu(bpy) complex.

In various embodiments, the amount of ligand metal complex, e.g., Cu(bpy) complex, is less than about 2 mM, or less than about 1.5 mM, or less than about 1 mM, or less than about 0.8 mM, or less than about 0.5 mM. In one embodiment, the ligand metal complex is about 1 mM. The amount of the ligand metal complex is reduced by at least about 25%, or by at least about 50% or by at least about 75% compared to oxidative pretreatment process with one oxidant.

Use of the multi-ligand metal complexes described herein also reduces the amount of metal, such as copper, used in the process as compared to a single-ligand metal complex, such as a single ligand copper complex, by at least 50%, or at least 40%, or at least 30% or at least 20% or at least 10% or at least 5% or lower, including any range therein. Use of a reduced amount of metal not only reduces toxicity levels, but further reduces costs.

Use of the multi-ligand metal complex may reduce the amount of oxidant, such as hydrogen peroxide and/or oxygen, used in the oxidative pretreatment by at least 90%, by at least 80%, by at least 70%, by at least 60%, by at least 50%, or at least 40%, or at least 30% or at least 20% or at least 10% or at least 5% or lower, including any range therein. Use of a reduced amount of oxidant further reduces costs.

In one embodiment, the pH of the plant biomass being pretreated is adjusted to increase the number of deprotonated groups. In one embodiment, the pH of the pretreated biomass is, or the biomass is pH adjusted to achieve, a neutral pH during the pretreatment process. In one embodiment, the pH is adjusted to achieve an alkaline pH to deprotonate the phenolic groups in lignin and to increase lignin solubility. In one embodiment, the pH is adjusted to at least 11, such as at least 11.5, including any value in between. In some embodiments, elevation of the pH is achieved with bases such as ammonia and/or ammonia derivatives, such as amines, in which copper is stabilized in solution in the form of a complex ion. In one embodiment, the pH is adjusted via addition of a base, which can react with lignin and cause depolymerization and/or solubilization, i.e., helps the plant cell wall to become degraded and/or destroyed, thus reducing resistance to subsequent hydrolysis.

In various embodiments, the ss-AHP/O process described herein includes the addition of base only once in the pretreatment process. In contrast, the two-stage process includes the addition of base in each of the steps. Advantageously, the total amount of base added in the ss-AHP/O process can be less than the amount of base added in the combined two stage process. In various embodiments, bases used in the ss-AHP/O include sodium hydroxide, ammonia, potassium hydroxide, and sodium carbonate.

In various embodiments, the amount of base added to the pretreatment process is less than about 30 percent w/w based on the dry weight of the original biomass. In one embodiment, the amount of base is less than about 25 percent, or less than about 20 percent, or less than about 15 percent based on the dry weight of the original biomass. In various embodiments, the amount of base added to the pretreatment process is at least about 10 percent based on the dry weight of the original biomass.

In one embodiment, the amount of base added in the ss-AHP/O can be about 15% of sodium hydroxide or less, w/w of the dry weight of the original biomass. In contrast, the two stage process can use about 10% of sodium hydroxide, w/w of the dry weight of the original biomass, in each of the two steps, resulting in the use of about 20% of sodium hydroxide total, w/w of the dry weight of the original biomass.

In one embodiment, the oxidants used in the ss-AHP/O process included hydrogen peroxide at about 2% w/w of the plant biomass and oxygen at about 300 psi and the amount of base used is at about 15% w/w of the original plant biomass. In one embodiment, the base is sodium hydroxide. Variations of this combination of concentrations may be used as described above and are within the scope of this description.

In various embodiments, the temperature at which the ss-AHP/O process is conducted can be increased to improve the economics of the pretreatment process. In various embodiments, the ss-AHP/O process is conducted at a temperature of about 60° C. or greater, or about 70° C. or greater, or about 80° C. or greater, or about 90° C. or greater, or about 100° C. or greater. In various embodiments, the ss-AHP/O process is conducted at a temperature of about 140° C. or less, or about 130° C. or less, or about 120° C. or less, or about 110° C. or less, or about 100° C. or less, or about 90° C. or less, or about 80° C. or less, or about 70° C. or less. In one embodiment, the ss-AHP/O process is conducted at a temperature of about 80° C.

In various embodiments, the ss-AHP/O process is conducted for about 48 hours or less. In one embodiment, the ss-AHP/O process is conducted for about 36 hours or less, or about 24 hours or less, or about 18 hours or less, or about 12 hours or less, or about 9 hours or less, or about 6 hours or less.

In one embodiment, the ss-AHP/O pretreatment process can be conducted at about 80° C. for about 3 hours to about 24 hours, or for about 8 hours to about 16 hours, or for about 10 hours to about 14 hours. Variation of these combinations of temperature and incubation time may be used and are within the scope of this description.

Any suitable plant biomass can be used. In one embodiment, the plant biomass contains transition metals. Use of a plant biomass containing more than trace amounts of one or more transition metals results in further cost savings, as a reduced amount of catalyst is needed to affect the same or substantially the same results. Examples of plant biomass containing more than trace amounts of transition metals include, but are not limited to, hardwoods of the genus *Populus* (e.g., various types of poplar including hybrid poplar, hybrid aspen, western balsam poplar, and the like), birch (including silver birch and the like), maple (including sugar maple and the like), further including grasses (including, but not limited to, corn, switchgrass, sorghum, *miscanthus*) and gymnosperms, which are also referred to as conifers and softwoods (including, but not limited to, the genus of *Pinus*, such as *Pinus resinosa*, i.e., red pine).

In one embodiment, the plant biomass contains one or more transition metals that are redox-active, including, but not limited to, Fe, Mn, Cr, Co, Ni, Cu, Mo, Pd, Ru, Re, Pt, Pd, Os, Jr and combinations thereof.

In various embodiments, the biomass may be subjected to a cycle of hydrolysis (e.g., enzymatic, acid, etc.) using any conventional methods known in the art. In one embodiment, a reduced amount of enzymes is used, as compared to hydrolysis of conventionally catalyzed pretreated biomass.

In various embodiments, use of a ss-AHP/O process, as described herein provides improved downstream bioproduct yields, such as sugar yields and lignin yields, as compared to yields obtained in the two-stage, two oxidant process as shown, for example, below in the Examples.

In various embodiments, the amount of solubilized lignin from the plant biomass can be similar or improved relative to a two-stage, dual oxidant process. In one embodiment, the amount of solubilized lignin in the ss-AHP/O process was at least 50%, or at least 60%, or at least 70%, or at least 75%, or at least 80% of the lignin in the plant biomass.

In various embodiments, the overall sugar release following the enzymatic hydrolysis can be similar or improved relative to a two-stage, dual oxidant process. In one embodiment, in the ss-AHP/O process, the overall glucose yield was at least 60%, or at least 70%, or at least 75%, or at least 80%, or at least 90%, or at least 95%, or at least 98%, or at least 99%, or 100% of glucan in the plant biomass. In one embodiment, in the ss-AHP/O process, the overall xylose yield was at least 60%, or at least 70%, or at least 75%, or at least 80%, or at least 90%, or at least 95%, or at least 98%, or at least 99%, or 100% of xylose in the plant biomass.

In one embodiment, yields may be improved compared to a two-stage, two oxidant process by at least about 5% or higher, such as at least about 10% or higher, at least about 20% or higher, at least about 30% or higher, at least about 40% or higher, at least about 50% or higher, up to two or three times higher, including any range there between.

In one embodiment, the use of ss-AHP/O process can result in using lower amounts of enzymes for enzymatic hydrolysis of the catalytically pretreated biomass than the catalytically treated biomass generated from a two-stage, two oxidant process. In various embodiments, the amount of enzyme used for hydrolysis is less than about 50 mg protein/g glucan, or less than about 40 mg protein/g glucan, or less than about 30 mg protein/g glucan, or less than about 20 mg protein/g glucan, or less than about 15 mg protein/g glucan, or less than about 10 mg protein/g glucan. In various embodiments, the amount of enzyme used for hydrolysis is more than about 5 mg protein/g glucan, or more than about 10 mg protein/g glucan, or more than about 15 mg protein/g glucan, or more than about 20 mg protein/g glucan, or more than about 25 mg protein/g glucan. In one embodiment, the amount of enzyme used for hydrolysis is about 15 mg protein/g glucan.

In various embodiments, the overall monomeric sugar yields following enzymatic hydrolysis in the ss-AHP/O process increased compared to a two-stage, two oxidant process. In various embodiments, the amount of xylose yield (based on the initial sugar composition in the plant biomass) is more than about 70%, or more than about 80%, or more than about 90%, or more than about 95%, or about 100%. In various embodiments, the amount of xylose yield (based on the initial sugar composition in the plant biomass) is about 100% or less, or about 95% or less, or about 90% or less, or about 85% or less.

In various embodiments, the amount of glucose yield (based on the initial sugar composition in the plant biomass) is more than about 70%, or more than about 80%, or more than about 90%, or more than about 95%, or about 100%. In various embodiments, the amount of glucose yield (based on the initial sugar composition) is about 100% or less, or about 95% or less, or about 90% or less, or about 85% or less. In one embodiment, the amount of glucose yield is about 93% and the amount of xylose yield is about 100% (based on the initial sugar composition in the plant biomass).

Use of the metal-ligand complexes in a ss-AHP/O process described herein also reduces the amount of metal, such as copper, and the amount of ligand, e.g. bpy, used in the process as compared to a two-stage, two oxidant process, by at least 75%, or by at least 50%, or at least 40%, or at least 30% or at least 20% or at least 10% or at least 5% or lower, including any range therein. Use of a reduced amount of metal and ligand can reduce costs and can reduce toxicity.

Use of a ligand-metal complex in a ss-AHP/O process may reduce the amount of the one of the more expensive oxidants, e.g. hydrogen peroxide, used compared to other oxidative treatments by at least 80%, or by at least 70%, or by at least 60%, or by at least 50%, or by at least 40%, or by at least 30% or by at least 20% or by at least 10% or by at least 5% or lower, including any range therein. Use of a reduced amount of oxidant further reduces costs.

Use of alkaline, e.g., sodium hydroxide, in a single stage dual oxidant process, e.g., ss-AHP/O process, may reduce the amount of alkaline used in the biomass pretreatment process compared to the two stage, two oxidant process by at least about 50%, or at least about 40%, or at least about 30%, or at least about 25%, or at least about 20%, or at least about 15%, or at least about 10%. Use of a reduced amount of alkaline further reduces costs.

An additional benefit relates to reduced microbial toxicity. Microbial toxicity is characterized by the final growth of yeast cells during yeast fermentation, and/or the growth rate of yeast during fermentation, and/or the length of the lag phase during fermentation. Such toxicity is caused by metal ions and other chemicals present in the processing stream, including the metals present in the multi-ligand catalyst and metal elements present in the plant biomass itself. Since the various embodiments allow for a reduced amount of metal as compared to conventional processes, the yeast used downstream is less adversely affected down to minimally adversely affected. As such, in one embodiment, the multi-ligand complexes have minimal microbial toxicity towards yeast fermentation (i.e., less than 50% reduction in final growth of yeast cells, as quantified with optical density).

In various embodiments, hydrolysis may optionally be followed by or integrated with either fermentation or sugar catalytic conversion of sugars to bioproducts, such as biofuels, biochemicals and biopolymers. In one embodiment, such yields may be improved by at least 5% or higher, such as at least 10%, at least 20%, at least 30%, at least 40% at least 50% or higher, up to two or three times higher, including any range there between.

In various embodiments, the use of two oxidants in the single-stage oxidative pretreatment process can result in favorable technoeconomic analysis (TEA) of the pretreatment of biomass to generate biofuels. In various embodiments, the improved TEA can result from conducting the pretreatment process in a single stage, conducting the ss-AHP/O process at a higher temperature, using two oxidants, hydrogen peroxide and oxygen, in conjunction with a single-ligand metal complex, e.g. Cu(bpy), reducing the amount of ligand used in the oxidative pretreatment process, reducing the load of the enzyme in the enzymatic hydrolysis with improved yield of monomeric sugars and/or a combination of these factors.

In one embodiment, improved TEA can result from conducting the pretreatment of the biomass in a single stage without a separate alkaline pre-extraction step, conducting the ss-AHP/O pretreatment process at about 80° C., using hydrogen peroxide and oxygen as oxidants in conjunction with Cu(bpy), and reducing the amount of the ligand to 1 mM, reducing the amount of hydrogen peroxide to 2% w/w ($H_2O_2$/original biomass) with oxygen at about 300 psi, reducing the load of the enzyme to 15 mg protein/g glucan in the enzymatic hydrolysis leading to an improved yield of monomeric sugars, e.g. about 93% glucose and about 100% xylose (based on the initial sugar composition in the plant biomass).

TEA indicates that the improved conditions can reduce the minimum fuel selling price (MFSP) compared to a two-stage, two oxidant process (Cu-AHP/O) by more than about 20%, or by more than about 30%, or by more than about 40%, or by more than about 50%, or by more than about 60%. In one embodiment, TEA indicates that the improved conditions can reduce the MFSP by about 30% to about 40% compared to a two-stage, two oxidant process using $H_2O_2$.

TEA indicates that the improved conditions can reduce the minimum fuel selling price (MFSP) compared to a one-stage one oxidant process (conventional-AHP) by more than about 20%, or by more than about 30%, or by more than about 40%, or by more than about 50%, or by more than about 60%, or by more than about 70%, or by more than about 80%, or by more than about 90%. In one embodiment, TEA indicates that the improved conditions can reduce the MFSP by about 30% to about 40% compared to a one-stage one oxidant process using $H_2O_2$.

In one embodiment, the process can further include recovery and reuse of the ligand metal complex, including recovery of the metal itself. Conventional technologies for metal removal (e.g., copper) from wastewater streams are based on ion exchange, precipitation/co-precipitation plus filtration, and membrane separation. Additionally, lignocellulose such as waste biomass or biomass fractions, such as lignin, have been proposed as biosorbant materials in the treatment of wastewater to remove heavy metals, including copper. Cationic metals can sorb to charged anionic groups such as deprotonated phenolic hydroxyls in lignin or carboxylate groups in lignin or uronic acids in pectins and hemicellulose and are known to be strongly affected by pH with more deprotonated groups at elevated pH.

In one embodiment, catalyst sorption to biomass is strongly pH-dependent with near-complete catalyst adsorption to biomass at alkaline pH and substantial desorption at neutral to acidic pH. In one embodiment, pH is adjusted to recover the multi-ligand metal complex. In one embodiment, untreated plant biomass is used as an adsorbent to both recover the catalyst and impregnate the catalyst into the untreated plant biomass (such as woody biomass, including, but not limited to, poplar, hybrid polar, and other trees).

In one embodiment, any conventional method is used to recover the catalyst from either the unhydrolyzed pretreated biomass (often referred to as "pretreatment liquor") and/or the clarified (cell-free) stillage following fermentation and distillation. Such methods include, but are not limited to, flocculation, precipitation, and filtration using a polyanionic flocculant (e.g., Betz-Dearborn MR2405 or Ondeo-Nalco 8702) which is commercially employed to remove heavy metals during wastewater treatment. Such methods can further include recovery by adsorption to a commercial ion exchange resin (e.g., Amberlyst™ 40Wet) which is used industrially to recover and recycle copper catalyst used in the production of adipic acid. In one embodiment, the catalyst is recovered and recycled.

In embodiments which include a sugar conversion step, recovery and reuse of the ligand metal complex provides the additional benefit of further reducing toxicity during subsequent sugar conversion steps. Recovering and recycling the ligand metal complex further helps to reduce costs.

In one embodiment, the process may produce monomeric aromatic compounds, such as, syringic acid, vanillin, syringaldehyde acid, vanillic acid. Such aromatic compounds are useful in a number of applications, such as food additives, polymer precursors, and several types of chemicals.

In one embodiment, the process may produce aliphatic acids, including, but not limited to formic acid, oxalic acid, acetic acid, lactic acid, succinic acid, azaleic acid. Such aromatic compounds are useful in a number of applications, such as food additives, polymer precursors, and fine chemicals.

The various embodiments will be further described by reference to the following examples, which are offered to further illustrate various embodiments. It should be understood, however, that many variations and modifications may be made while remaining within the scope of the various embodiments.

Example 1

Materials—The hybrid poplar (*Populus nigra* var. *charkoviensis* x *caudina* cv. NE-19), obtained from the University of Wisconsin Arlington Agricultural Research Station, was harvested in 2012. The air-dried wood logs were chipped and hammer-milled (HammerHead, Muson Co., Inc. USA) to pass through a 5-mm screen. The milled biomass was stored in airtight bags prior to use. The chemical composition analysis of the biomass was 45.5% glucan, 15.8% xylan (sum of xylan, galactan, and manan), 22.3% Klason lignin, 9.5% acid soluble lignin, 3.2% extractives, and 0.85% ash. The enzyme cocktails Cellic CTec3 (197.3 mg/g) and HTec3 (170.5 mg/g) were kindly provided by Novozymes A/S (Bagsværd, Denmark). All other chemicals were reagent grade and purchased from Fisher Scientific (USA) unless otherwise noted.

Single-stage Cu-AHP pretreatment—The single stage $O_2$-enhanced Cu-AHP pretreatment was conducted using a 100-mL stainless steel Parr reactor (Parr Instruments Company, Moline, IL, USA) at a biomass loading of 10% (w/v) (based on the weight of original biomass). The oxidative pretreatment was performed with several fixed conditions, including 1 mM $CuSO_4$ (0.159% w/w, based on original biomass) and 1 mM 2,2'-bipyridine (bpy) (0.156% w/w, based on original biomass). For each experiment, 5 g (dry basis) of hybrid poplar, 49.7 mL of a NaOH aqueous solution (including deionized water, 2.5 or 3.75 mL of 5 M NaOH, catalyst, and $H_2O_2$) were incubated at 200 rpm for 6-24 h. The reactions were performed at 80-110° C. with the $H_2O_2$ loading of 2-8% (w/w) (based on the dry weight of original biomass) and the $O_2$ pressure of 100-300 psi (689-2068 kPa). After reaction, the reactor was quenched in an ice/water bath and depressurized at room temperature. Then, the solid fraction was separated from the liquor via filtration. The solid was washed with deionized water and stored at 4° C. for compositional analysis and enzymatic hydrolysis. The liquid phase was subjected to lignin precipitation by acidification with 72% (w/w) $H_2SO_4$. After reducing the pH to 2.0, the precipitate was recovered by centrifugation (10 min at 11269×g). After washing, the precipitate (lignin) was frozen at −80° C., lyophilized, and stored in the dark at 4° C.

Enzymatic hydrolysis—Enzymatic hydrolysis was performed using 15-mL Falcon tubes at 5% (w/v) solid loading (based on the weight of original, untreated biomass) and 50° C. for 72 h in 50 mM sodium citrate buffer (pH 5) with orbital shaking at 80 rpm (C24KC Incubator Shaker, New Brunswick Scientific, NJ, USA). The enzyme loading was 15 mg protein/g glucan (based on initial glucan content) using an enzyme cocktail consisting of CTec3 and HTec3 at a protein ratio of 1:1. Following enzymatic hydrolysis, the reaction mixture was centrifuged for 10 min at 3075×g to separate liquid phase. The concentration of glucose and xylose released into solution was measured using a high-performance liquid chromatography (HPLC) system (Agilent 1260 Series) following a National Renewable Energy Laboratory (NREL) protocol.

Chemical composition analysis—The moisture content of the biomass was determined by drying at 105±2° C. to a constant weight. Before and after the pretreatment, the chemical composition of biomass was measured following an NREL two-stage hydrolysis protocol. In brief, the air-dried biomass was ground with a Wiley Mill to pass through 20 mesh screen. A sample (0.1 g) of the ground material was digested by the two-step $H_2SO_4$ hydrolysis protocol. After hydrolysis, the acid-insoluble lignin (Klason lignin) was separated by filtration, dried at 105±2° C., and weighed. The content of carbohydrates was quantified by an HPLC system (Agilent 1260 Series equipped with an infinity refractive index detector) fitted with a Bio-Rad Aminex HPX-87H column (Bio-Rad Laboratories, USA) using 5.0 mM sulfuric acid as the mobile phase with a flow rate of 0.6 mL min$^{-1}$ and an operation temperature of 65° C. The xylose content reported is the combination of xylose, mannose, and galactose because the HPX-87H column cannot separate these three sugars. Sugar quantification was accomplished by comparing the peak area to a standard curve prepared using pure glucose and xylose.

Lignin characterization—The hydroxyl content of the lignin samples was measured using phosphorous-31 nuclear magnetic resonance ($^{31}P$ NMR) spectroscopy. Approximately 40 mg of the dry lignin was dissolved in 325 μL of a mixture of anhydrous pyridine and $CDCl_3$ (volume ratio of 1.6:1) and 300 μL anhydrous dimethylformamide (DMF). After completely dissolving the lignin, 100 μL cyclohexanol (stock concentration of 22 mg/mL) in anhydrous pyridine and $CDCl_3$ (volume ratio of 1.6:1) was added into the solution as an internal standard. Chromium (III) acetylacetonate (50 μL of a 5.6 mg/mL stock solution) in anhydrous pyridine and $CDCl_3$ (volume ratio of 1.6:1) was added into the mixture as a relaxation reagent. Phosphorylation of the lignin hydroxyl groups was initiated by the addition of 100 μL of the phosphitylation reagent 2-chloro-4,4,5,5-tetramethyl-1,3,2-dioxaphospholane. Analysis of the solution was performed using an Agilent DDR2 500 MHz NMR spectrometer (relaxation delay of 5 s and 128 scans) equipped with a 7600AS autosampler and VnmrJ 3.2A software. After obtaining the $^{31}P$ NMR spectra, the hydroxyl content of the lignin sample was calculated based on the ratio of the cyclohexanol internal standard (145.3.1-144.9 ppm) peak areas to the sample peak areas as described by Brandt et al.

To evaluate the appropriateness of using the lignin in polyurethane formulations, the reactivity of the lignin towards isocyanate (a key reagent that reacts with polyols in the manufacture of polyurethane) was tested. The reactivity of the lignin was determined using a titration method following a modified version of the American Society for Testing and Materials standard ASTM-D5155-14. Briefly, 1.0 g of methylene diphenyl diisocyanate (MDI) and 1.0 g of oven-dried lignin were dissolved in 6.0 g of DMF (dried with 4 A molecular sieves, Fisher Scientific) and heated at 50° C. for 60 min. Then, 0.5 g of the solution was added to 25 mL of a dibutylamine solution (2 M) in toluene and mixed at 23° C. for 15 min at 150 rpm, followed by the addition of 110 mL of 2-propanol. After mixing, the solution was titrated with 1 M HCl to pH 4.2. A separate experiment was performed without the addition of the lignin-isocyanate sample as the control. Polyethylene glycol 400 (PEG 400) was used as a reference petroleum-based polyol. The amount of free isocyanate (unreacted isocyanate) was calculated according to equation (1):

$$\%NCO = \frac{4.202(V_1 - V_2) \times M}{m} \quad (1)$$

where % NCO is the fraction of free (unreacted) isocyanate, $V_1$ is the volume of HCl required to reach pH 4.2 for the control sample (mL), $V_2$ is the volume of HCl required to reach pH 4.2 for lignin-isocyanate sample (mL), M is the molarity of HCl, and m is the weight (g) of the lignin/isocyanate sample added to the analysis mixture.

$^1H$-$^{13}C$-gradient heteronuclear single quantum coherence (HSQC) spectra were recorded on a 500 MHz Bruker NMR spectrometer equipped with a 5 mm iProbe (BBO probe) at room temperature using pulse sequence "hsqcedetgp-sisp2.3". Spectra were recorded with spectral widths of 8013 Hz ($^1H$) and 20 kHz ($^{13}C$) with an acquisition time of 63.9 ms (F2, 512 complex points for $^1H$) and 63.9 ms (F1, 1024 increments for the $^{13}C$ dimension) and 48 scans were taken per increment using a delay of 1.5 s.

Depolymerization of lignin—Lignin oxidation was conducted using the lignin oxidation and depolymerization (LOAD) process described in Alherech, M. et al. *ACS Cent. Sci.* 2021, vol. 11, pp. 1831-1837, incorporated herein by reference. Briefly, to a hollowed, 100 mm tall, 26 mm O.D., and 24 mm I.D. PTFE vial were added a 1.5 mm×7.9 mm PTFE coated stir bar, 50 mg of lignin, 10 mL 2 M aqueous sodium hydroxide, and 3.3 mg $CuSO_4·5 H_2O$. The solution was stirred at room temperature until the lignin dissolved while 115 mL of water as a heating medium was added to a 1-L, stainless steel Parr reactor. The PTFE tube containing the reaction contents was placed in a 1-L stainless steel vessel. The Pan vessel was wrapped with a heating mantle, affixed to a stir plate, sealed with a lid bearing a pressure gauge and thermocouple, then protected with a blast shield. The stirring was turned on and the reactor was pressurized to 25 bar with air. The heating mantle and thermocouple were connected to a Parr 4838 Reaction Controller tuned to a 175° C. set point and turned on to heat the reactions. After 45 minutes, when the reaction reached 160° C., the heating was turned off and the reactor was submerged in a bucket of ice. When the reaction temperature fell to below 45° C., the pressure was released and the reactor was opened. The contents of the PTFE tube were acidified with concentrated HCl until the solution became cloudy and was extracted with ethyl acetate (3×5 mL). The ethyl acetate solutions were combined and concentrated by rotary evaporation until a dark residue remained.

Results and Discussion

Figure 2:
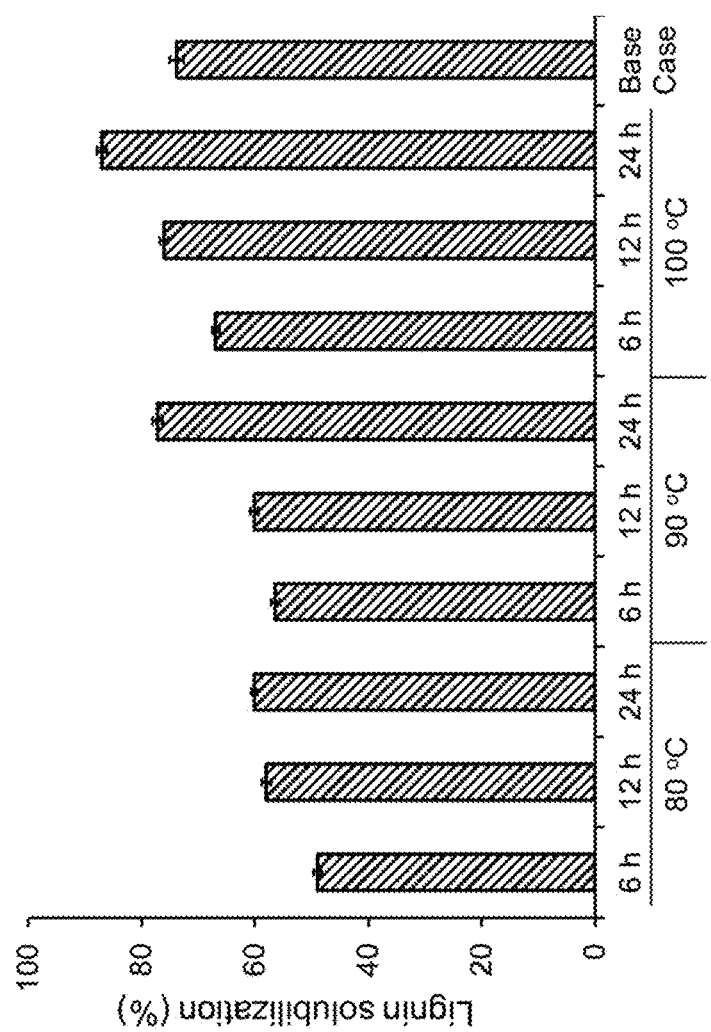
FIG. 2 is a plot of the effect of pretreatment temperature and time on lignin solubilization.

Alkaline-oxidative pretreatment condition investigation—To examine the performance of the single-stage alkaline-oxidative pretreatment, reactions with original biomass were performed. The first series of reactions were performed with 8% $H_2O_2$ and 300 psi $O_2$. FIG. 2 shows the effect of reaction temperature and time on the solubilization of lignin. The base case (FIG. 2) was the biomass pretreated following the two-stage alkaline pre-extraction (120° C., 10% NaOH, 1 h)/alkaline-oxidative pretreatment (80° C., 10% NaOH, 1 mM Cu, 1 mM 2,2'-bipyridine, 2% $H_2O_2$, 50 psi $O_2$, 12 h) process (Yuan et al., 2021). As shown, with increasing the pretreatment severity, the amount of solubilized lignin increased. Under the most severe conditions investigated (100° C., 24 h), about 80% of original lignin was solubilized, which was even higher than the two-stage pretreatment process (base case, ~75%). The solubilization of such high amount of lignin has the potential to generate biomass with high enzymatic digestibility.

Figures 3A, 3B:
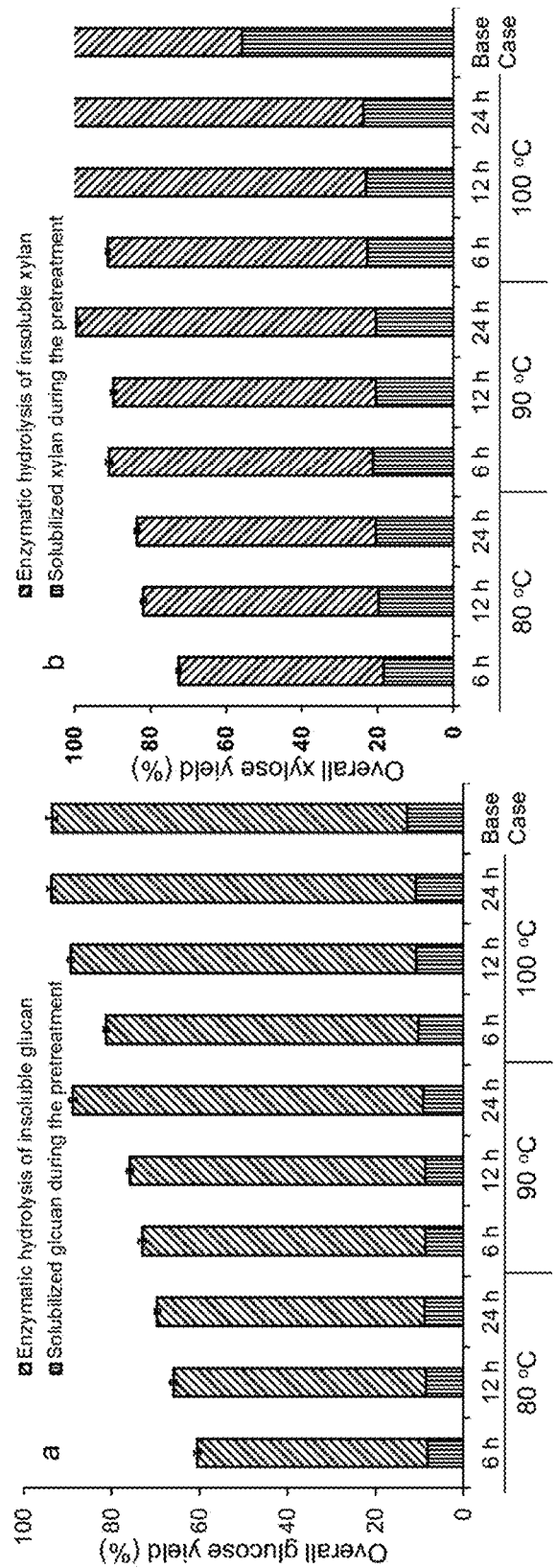
FIG. 3A is a plot of the effect of pretreatment temperature and time on overall glucose release.
FIG. 3B is a plot of the effect of pretreatment temperature and time on overall xylose release.

FIGS. 3A-3B shows the overall sugar release following enzymatic hydrolysis. As shown in FIG. 3A, when increasing the single-stage alkaline-oxidative pretreatment severity, the overall glucose yield (~95%) was similar to that of the two-stage alkaline pre-extraction/alkaline-oxidative pretreatment process. Also, the xylose yield was close to 100% (based on initial xylan content). Based on the results shown in FIGS. 2, 3A and 3B, the pretreatment conditions under temperature of 100° C. and time of 24 h were selected for the following study.

Figure 4:
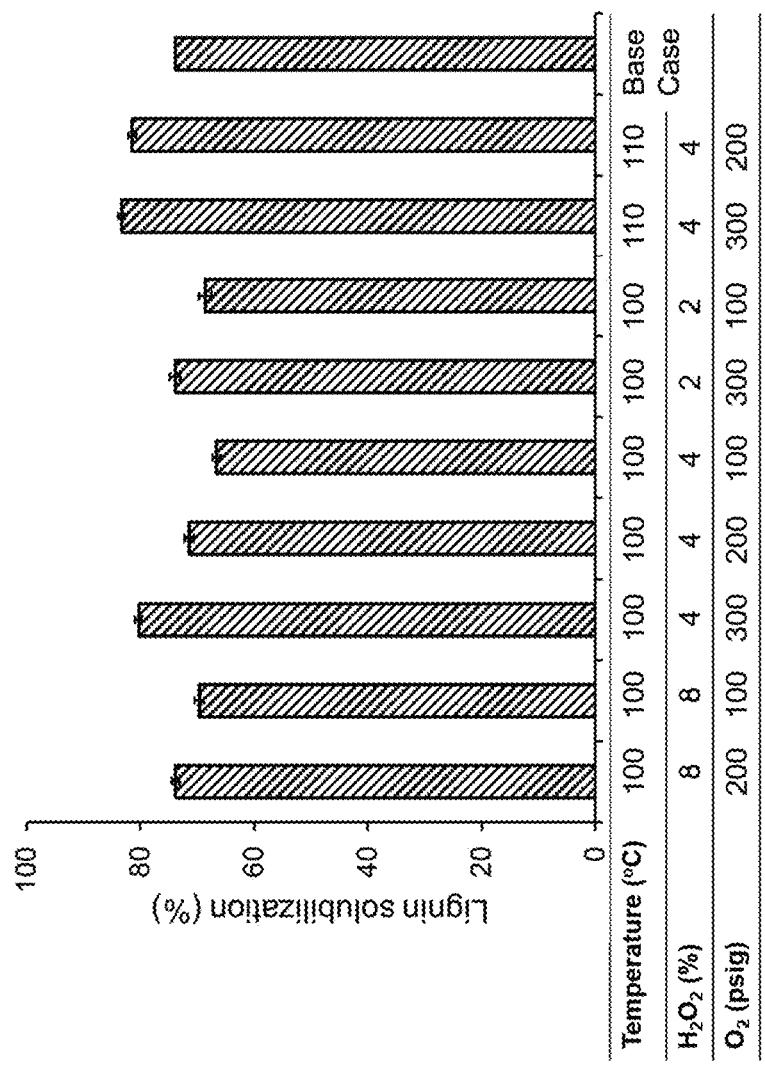
FIG. 4 is a plot of the effect of pretreatment temperature, $H_2O_2$ loading, and $O_2$ pressure during the Cu-AHP/O pretreatment on the solubilization of lignin.

Since the $H_2O_2$ loading (8% w/w) and $O_2$ pressure (300 psi) were high under the preliminary screening conditions (FIGS. 2, 3A and 3B), the possibility of reducing these inputs during the single-stage alkaline-oxidative pretreatment was investigated. FIG. 4 shows the solubilized lignin under various studied conditions with reduced $H_2O_2$ loading and $O_2$ pressure. As shown in FIG. 4, when reducing the pretreatment severity, the lignin solubilization decreased. However, when performing the Cu-AHP pretreatment with 4% $H_2O_2$ and 300 psig $O_2$ pressure, the lignin solubilization was still around 80% (based on initial lignin). To further reduce the $O_2$ pressure (from 300 psig to 200 psig) while maintaining the solubilization of such high amount of lignin, the temperature of the pretreatment needed to be increased to 110° C.

Figures 5A, 5B:
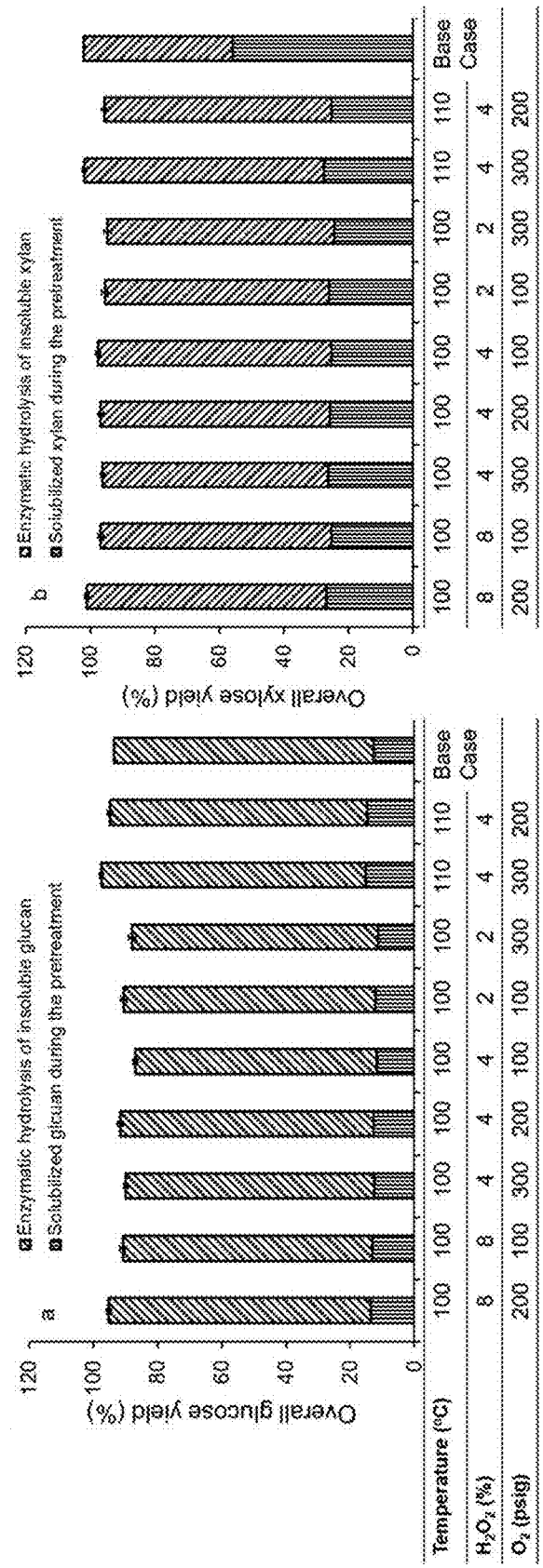
FIG. 5A is a plot of the effect of pretreatment temperature, $H_2O_2$ loading, and $O_2$ pressure during the Cu-AHP pretreatment on overall glucose yields.
FIG. 5B is a plot of the effect of pretreatment temperature, $H_2O_2$ loading, and $O_2$ pressure during the Cu-AHP pretreatment on overall xylose yields.

FIGS. 5A-5B show the overall sugar yields following enzymatic hydrolysis of the pretreated biomass. As shown, the overall glucose yields (FIG. 5A) could still reach ~95% (based on initial glucan content) when reducing both the $H_2O_2$ loading (from 8% to 4%) and the $O_2$ pressure (from 300 psig to 200 psig).

Technoeconomic Analysis (TEA) of the Single-Stage Cu-AHP Pretreatment

TEA analysis was conducted under different conditions as indicated below in Table 2 and Table 3. 5 mm NE-19 poplar was used as the raw biomass for all the runs in the Experiment series #1-9.

Experiment Series 1: #1-#9

Pretreatment conditions: one-stage $O_2$—Cu-AHP pretreatment at some fixed conditions: 15% (w/w) NaOH loading, 8% (w/w) $H_2O_2$, 1 mM Cu(bpy), 300 psi $O_2$ (Table 2). The time and/or temperature of the pretreatment process was varied in the various runs. Enzymatic hydrolysis: 15 mg protein/g glucan, 72 h, 50° C., pH 5.

Figure 6:
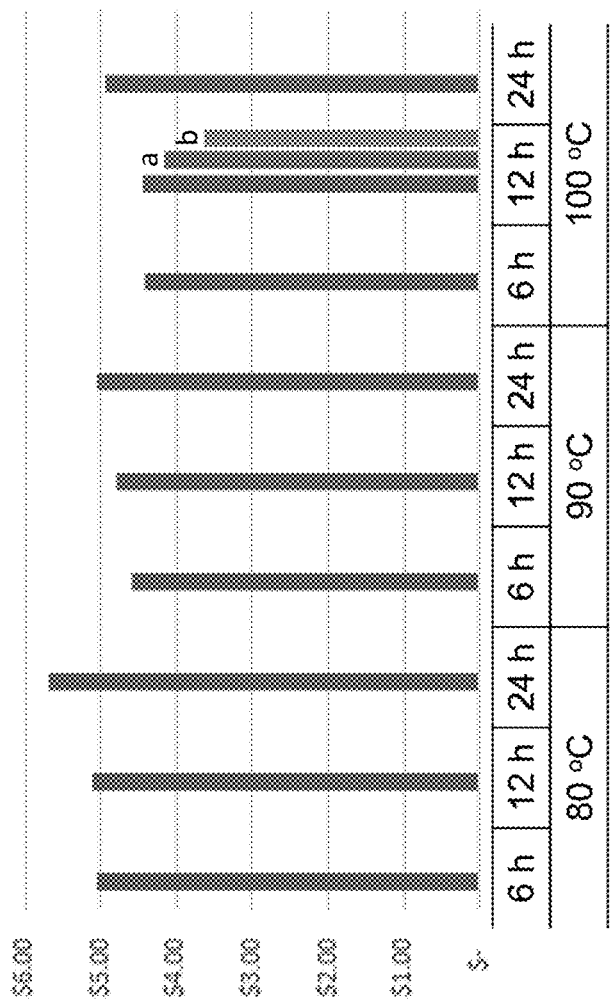
FIG. 6 is a plot of the effect of pretreatment temperature and time on minimum fuel selling price (MFSP) for Experiments #1-9.

Table 2 and FIG. 6 shows the sugar hydrolysis yields and technoeconomic analysis results for a number of conditions (Experiment series 1: #1-#9). Table 2 also shows sugar yields following enzymatic hydrolysis of $O_2$—Cu-AHP pretreated poplar under different conditions.

TABLE 2

| Run # | Temperature (° C.) | $H_2O_2$ loading (%) | $O_2$ pressure (psi) | Time (h) | Sugar yields %[a] | |
|---|---|---|---|---|---|---|
| | | | | | Glucose | Xylose |
| 1 | 80 | 8 | 300 | 6 | 52.3 ± 0.8 | 53.9 ± 1.2 |
| 2 | 80 | 8 | 300 | 12 | 57.4 ± 1.1 | 61.9 ± 1.2 |
| 3 | 80 | 8 | 300 | 24 | 60.8 ± 1.2 | 63.0 ± 0.9 |
| 4 | 90 | 8 | 300 | 6 | 64.4 ± 1.4 | 69.6 ± 1.4 |
| 5 | 90 | 8 | 300 | 12 | 67.1 ± 1.3 | 69.1 ± 1.1 |
| 6 | 90 | 8 | 300 | 24 | 79.7 ± 1.1 | 78.9 ± 0.9 |
| 7 | 100 | 8 | 300 | 6 | 70.9 ± 0.8 | 68.4 ± 0.8 |
| 8 | 100 | 8 | 300 | 12 | 78.6 ± 0.8 | 78.0 ± 0.8 |
| 9 | 100 | 8 | 300 | 24 | 82.8 ± 1.0 | 78.2 ± 0.9 |

[a]based on original sugar composition

Table 2 shows that higher sugar yields can be obtained at higher temperatures and incubation times. FIG. 6 shows that the MFSP can be reduced with a process using higher temperature and shorter reaction times. At 12 hours and 100° C., FIG. 6 also illustrates (bars (a) and (b)) that the MFSP can be even lower based on different assumptions for lignin. The value of acid insoluble lignin, the value of lignin being used as polyurethanes and the value of lignin being used as aromatic monomers can lead to lower MFSP.

Experiment Series 2: #10-#18

This is a set of one-stage $O_2$—Cu-AHP pretreatment process (no alkaline pre-extraction stage). Fixed experimental conditions: 15% (w/w) NaOH loading, 1 mM Cu(bpy), 24 h. Experiments were performed in triplicate.

Enzymatic hydrolysis: 15 mg protein/g glucan, 72 h, 50° C., pH 5.

Figure 7:
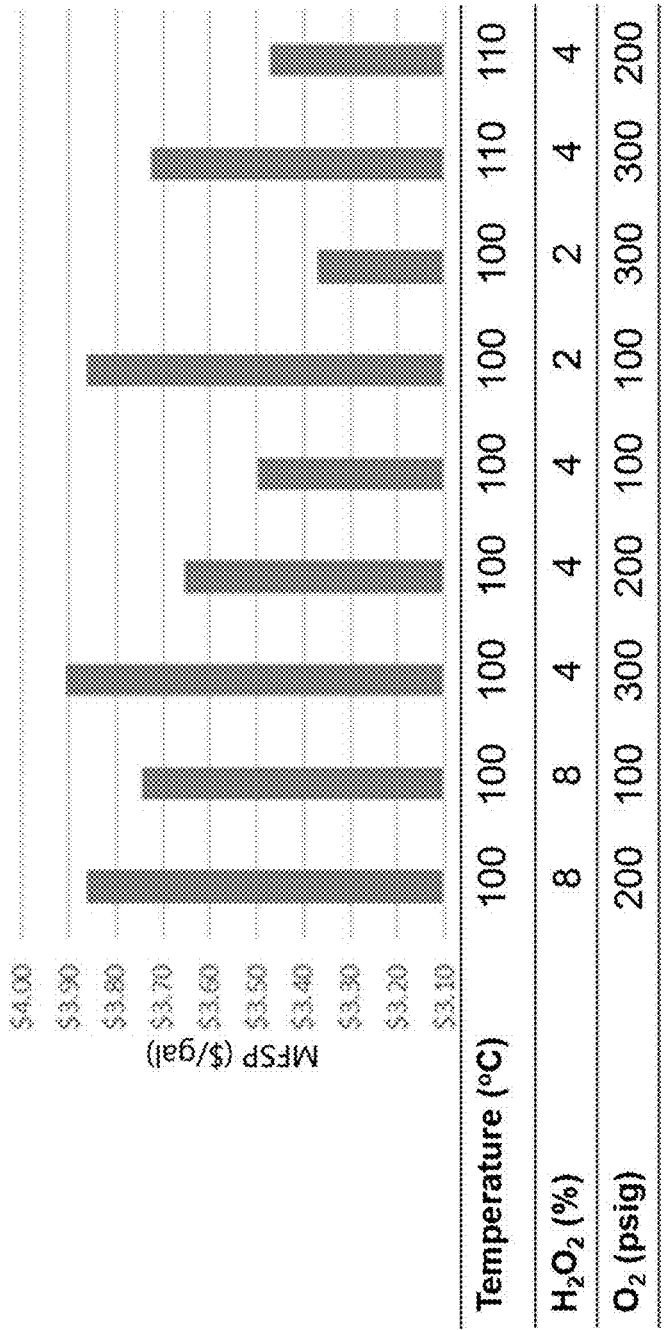
FIG. 7 is a plot of the effect of pretreatment temperature, $H_2O_2$ loading, and $O_2$ pressure during the Cu-AHP pretreatment on MFSP for Experiments #10-18. It was assumed that precipitated lignin is sold as polyol replacement at $0.8/kg.

TEA of samples #10-18 is shown in FIG. 7 and Table 3. Conditions are as indicated for #10-18. Assumption: precipitated lignin is sold as polyol replacement at $0.8/kg.

Costs of the samples #10-18. $O_2$ pressure was taken into consideration.

Table 3 shows sugar yields following enzymatic hydrolysis of one-stage $O_2$—Cu-AHP pretreated poplar under different conditions.

TABLE 3

| Run # | Temperature (° C.) | $H_2O_2$ loading (%) | $O_2$ pressure (psi) | Sugar yields %[a] | |
|---|---|---|---|---|---|
| | | | | Glucose | Xylose |
| 10 | 100 | 8 | 200 | 82.2 ± 1.3 | 75.1 ± 0.9 |
| 11 | 100 | 8 | 100 | 78.6 ± 1.1 | 72.4 ± 0.8 |
| 12 | 100 | 4 | 300 | 79.9 ± 1.2 | 69.9 ± 0.5 |
| 13 | 100 | 4 | 200 | 79.2 ± 1.2 | 70.5 ± 0.4 |
| 14 | 100 | 4 | 100 | 77.8 ± 1.4 | 71.8 ± 1.3 |
| 15 | 100 | 2 | 300 | 79.1 ± 0.9 | 70.9 ± 1.2 |
| 16 | 100 | 2 | 100 | 76.9 ± 0.7 | 70.6 ± 0.8 |
| 17 | 110 | 4 | 300 | 83.4 ± 0.9 | 73.7 ± 1.4 |
| 18 | 110 | 4 | 200 | 81.5 ± 1.5 | 71.3 ± 0.6 |

[a]based on original sugar composition

The oxygen pressure, the temperature and $H_2O_2$ loading were varied and the effect of MFSP was calculated. FIG. 7 shows the effect of MFSP under different conditions. The MFSP is the lowest for run #16. The sugar yields are greater for runs #17 and #18 than for #16 with slight increases in MFSP.

Figure 8:
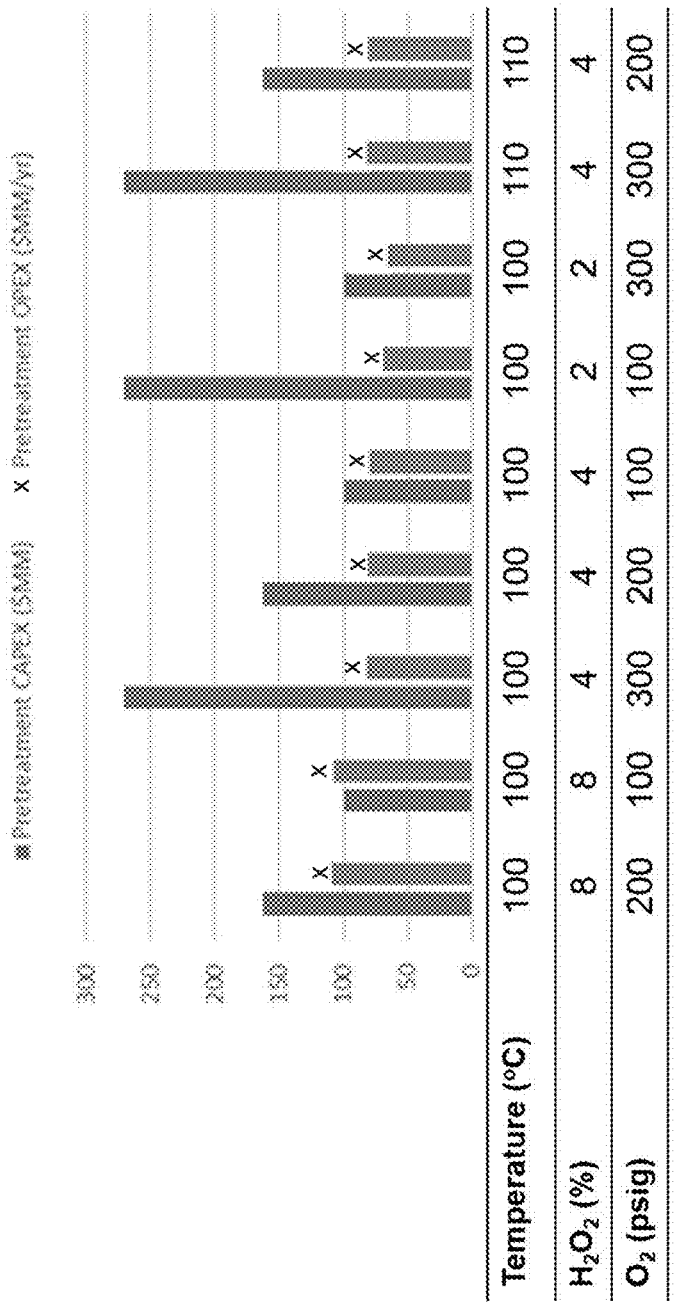
FIG. 8 is a plot of the effect of pretreatment temperature, $H_2O_2$ loading, and $O_2$ pressure during the Cu-AHP pretreatment on processing costs for experiments #10-18. $O_2$ pressure was taken into consideration. Pretreatment capital costs (CAPEX) and operating costs (OPEX) are shown. Bars with (x) refer to OPEX.

FIG. 8 is a plot of the effect of pretreatment temperature, $H_2O_2$ loading, and $O_2$ pressure during the Cu-AHP pretreatment on pretreatment capital costs (CAPEX) and operating costs (OPEX) (bars with (x) in FIG. 8) for experiments #10-18. These results show that the contributions of low CAPEX and OPEX for run #16, coupled with high sugar yields, are strong contributors to the low in MFSP in FIG. 7.

All publications, patents and patent documents are incorporated by reference herein, as though individually incorporated by reference, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. For example, although the process has been discussed using particular types of plant biomass, any type of plant biomass, such as grasses, rice straw and the like, for example, may be used. Additionally, although the process has been discussed using primarily copper as the metal in the multi-ligand metal catalyst, other metals, such as iron, in various oxidation states, for example, may be used. This application is intended to cover any adaptations or variations of the present subject matter. Therefore, it is manifestly intended that embodiments of this invention be limited only by the claims and the equivalents thereof.

What is claimed is:

1. A method of pretreating plant biomass comprising catalytically pretreating the plant biomass in a single-stage alkaline oxidative pretreatment process, wherein the process comprises providing a metal-ligand complex, providing a base and adding at least two oxidants to the alkaline oxidative pretreatment process to produce a catalytically pretreated plant biomass and wherein the method does not include an alkaline pre-extraction step prior to the alkaline oxidative pretreatment process.

2. The method of claim 1, wherein the oxidants are pressurized oxygen and hydrogen peroxide.

3. The method of claim 2, wherein the oxygen pressure is from 100 psi to about 400 psi and the hydrogen peroxide is less than about 6% (w/w).

4. The method of claim 1, wherein the at least two oxidants are present simultaneously in the pretreatment.

5. The method of claim 1, wherein the alkaline oxidative pretreatment is conducted at a temperature from about 90° C. to about 140° C.

6. The method of claim 1, wherein the method further comprises addition from about 5% to about 15% sodium hydroxide (w/w) to the alkaline oxidative pretreatment process.

7. The method of claim 1, wherein the metal-ligand complex comprises a second ligand.

8. The method of claim 1, wherein the catalytic pretreating step produces a liquid phase and the method further comprises:
    separating the catalytically pretreated biomass from the liquid phase to produce separated catalytically pretreated biomass; and
    hydrolyzing the separated catalytically pretreated biomass to produce hydrolyzed catalytically pretreated biomass.

9. The method of claim 8, wherein the hydrolyzing is conducted with an enzyme, wherein the enzyme is at a concentration from about 5 mg protein/g glucan to about 30 mg protein/g glucan.

10. A method of reducing cost in a homogenous catalytic reaction comprising catalytically pretreating plant biomass with a metal-ligand complex and at least two oxidants present in a single-stage alkaline oxidative pretreatment process to produce a catalytically pretreated plant biomass, hydrolyzing the catalytically pretreated biomass to produce hydrolyzed catalytically pretreated biomass for use as a biofuel, wherein the method does not include an alkaline pretreatment step prior to the alkaline oxidative pretreatment step.

11. The method of claim 10, wherein the oxidants are oxygen and hydrogen peroxide.

12. The method of claim 11, wherein the oxygen pressure is from about 100 psi to about 400 psi and the hydrogen peroxide is about 6% (w/w) or less.

13. The method of claim 10, wherein the metal-ligand complex comprises a second ligand.

14. The method of claim 10, wherein the alkaline oxidative pretreatment is conducted at a temperature from about 70° C. to about 120° C.

15. The method of claim 10, wherein the catalytic pretreating step produces a liquid phase and the method further comprises separating the catalytically pretreated biomass from the liquid phase to produce separated catalytically pretreated biomass.

16. The method of claim 10, wherein the method reduces the minimum fuel selling price (MFSP) by about 40% relative to the MFSP of a method using only hydrogen peroxide as the oxidant.

17. A method of pretreating plant biomass comprising catalytically pretreating the plant biomass in a single-stage alkaline oxidative pretreatment process, wherein the process comprises providing a metal-ligand complex and adding at least two oxidants to the alkaline oxidative pretreatment process to produce a catalytically pretreated plant biomass and wherein the one of at least two oxidants comprises pressurized oxygen at least 100 psi.

18. The method of claim 17, wherein the one of at least two oxidants further comprises hydrogen peroxide.

19. The method of claim 18, wherein the pressurized oxygen is from 100 psi to about 400 psi and the hydrogen peroxide is less than about 6% (w/w).

20. The method of claim 17, wherein the at least two oxidants are present simultaneously in the pretreatment.

* * * * *